United States Patent
Racenet et al.

(10) Patent No.: US 7,824,426 B2
(45) Date of Patent: Nov. 2, 2010

(54) DIRECTIONALLY BIASED STAPLES AND CARTRIDGE HAVING DIRECTIONALLY BIASED STAPLES

(75) Inventors: David C. Racenet, Litchfield, CT (US); Hanspeter Bayer, Meriden, CT (US); Scott Cunningham, Cheshire, CT (US)

(73) Assignee: Tyco Healthcare Group, LP, North Haven, CT (US)

( * ) Notice: Subject to any disclaimer, the term of this patent is extended or adjusted under 35 U.S.C. 154(b) by 1844 days.

(21) Appl. No.: 10/424,606

(22) Filed: Apr. 28, 2003

(65) Prior Publication Data

US 2004/0006372 A1 Jan. 8, 2004

Related U.S. Application Data

(63) Continuation of application No. 09/693,379, filed on Oct. 20, 2000, now abandoned.

(51) Int. Cl.
*A61B 17/08* (2006.01)
*A61B 17/04* (2006.01)

(52) U.S. Cl. .................... 606/219; 227/175.1

(58) Field of Classification Search .......... 606/75, 606/219, 220, 151; 227/175.1, 176.1, 177.1, 227/178.1, 179.1, 180.1; 411/457–461, 474
See application file for complete search history.

(56) References Cited

U.S. PATENT DOCUMENTS

| | | | |
|---|---|---|---|
| 30,896 A | 5/1899 | La Prelle | |
| 2,008,086 A * | 7/1935 | Sorenson | 411/474 |
| 2,122,814 A * | 7/1938 | Hansen | 411/457 |
| 2,128,443 A | 8/1938 | Vogel | |
| 2,153,874 A * | 4/1939 | Posnack | 411/457 |
| 3,490,675 A | 1/1970 | Green et al. | |
| 3,494,533 A | 2/1970 | Green | |
| 3,499,591 A | 3/1970 | Green | |
| 3,564,663 A | 2/1971 | Roberts | |
| 4,275,813 A | 6/1981 | Noiles | |
| 4,281,785 A | 8/1981 | Brooks | |
| 4,319,576 A | 3/1982 | Rothfuss | |
| 4,407,286 A | 10/1983 | Noiles et al. | |
| 4,425,915 A | 1/1984 | Ivanov | |
| 4,427,008 A | 1/1984 | Transue | |
| 4,438,769 A | 3/1984 | Pratt et al. | |
| 4,454,875 A | 6/1984 | Pratt et al. | |

(Continued)

FOREIGN PATENT DOCUMENTS

EP 0251444 A 1/1988

(Continued)

*Primary Examiner*—Julian W Woo

(57) ABSTRACT

In accordance with the present disclosure a directionally biased staple is provided for use in all types of surgical staplers having anvil structure against which the staple is formed. The directionally biased staple may be constructed in a wide variety of cross-sectional configurations including rectangular, elliptical, trapezoidal, etc. All of the configurations are distinguished by having a bending region requiring more force to twist or malform the staple than is required to properly form the staple. Preferably, these staples have Moment of Inertia Ratios on the order of between about 1.1 to about 3.0. The staple preferably corresponds in other respects to conventional formed staples, i.e. having at least a pair of leg members interconnected by a crown portion wherein the leg members are formed by direct contact with the anvil.

28 Claims, 33 Drawing Sheets

U.S. PATENT DOCUMENTS

| | | | |
|---|---|---|---|
| 4,467,805 | A | 8/1984 | Fukuda |
| 4,485,816 | A | 12/1984 | Krumme |
| 4,531,522 | A | 7/1985 | Bedi et al. |
| 4,534,351 | A | 8/1985 | Rothfuss et al. |
| 4,548,202 | A | 10/1985 | Duncan |
| 4,550,870 | A | 11/1985 | Krumme et al. |
| 4,589,582 | A | 5/1986 | Bilotti |
| 4,607,638 | A | 8/1986 | Crainich |
| 4,724,839 | A | 2/1988 | Bedi et al. |
| 4,741,336 | A | 5/1988 | Failla et al. |
| 4,747,531 | A | 5/1988 | Brinkerhoff et al. |
| 4,767,044 | A | 8/1988 | Green |
| D297,764 | S | 9/1988 | Hunt et al. |
| 4,787,387 | A | 11/1988 | Burbank, III et al. |
| 4,805,823 | A | 2/1989 | Rothfuss |
| 4,878,608 | A | 11/1989 | Mitsuhashi |
| 4,887,601 | A | 12/1989 | Richards |
| 4,955,898 | A | 9/1990 | Matsutani et al. |
| 4,978,049 | A | 12/1990 | Green |
| 5,007,921 | A | 4/1991 | Brown |
| 5,026,390 | A | 6/1991 | Brown |
| 5,219,353 | A | 6/1993 | Garvey, III et al. |
| 5,221,036 | A | 6/1993 | Takase |
| 5,222,975 | A | 6/1993 | Crainich |
| 5,242,457 | A | 9/1993 | Akopov et al. |
| 5,246,443 | A | 9/1993 | Mai |
| 5,342,396 | A | 8/1994 | Cook |
| 5,350,400 | A | 9/1994 | Esposito et al. |
| 5,354,306 | A | 10/1994 | Garvey, III et al. |
| 5,366,479 | A | 11/1994 | McGarry |
| 5,395,030 | A | 3/1995 | Kuramoto et al. |
| 5,413,584 | A | 5/1995 | Schulze |
| 5,415,334 | A | 5/1995 | Williamson, IV et al. |
| 5,445,648 | A | 8/1995 | Cook |
| 5,454,814 | A | 10/1995 | Comte |
| D364,462 | S | 11/1995 | Michelson |
| 5,480,089 | A | 1/1996 | Blewett |
| 5,486,187 | A | 1/1996 | Schenck |
| 5,489,058 | A | 2/1996 | Plyley et al. |
| 5,497,933 | A * | 3/1996 | DeFonzo et al. ......... 227/175.1 |
| D378,409 | S | 3/1997 | Michelson |
| 5,630,541 | A | 5/1997 | Williamson, IV et al. |
| 5,632,432 | A | 5/1997 | Schulze et al. |
| 5,702,048 | A | 12/1997 | Eberlin |
| 5,725,554 | A | 3/1998 | Simon et al. |
| 5,732,872 | A | 3/1998 | Bolduc et al. |
| 5,735,444 | A | 4/1998 | Wingert |
| 5,738,474 | A | 4/1998 | Blewett |
| 5,749,896 | A | 5/1998 | Cook |
| 5,758,812 | A | 6/1998 | Raffoni |
| 5,814,055 | A | 9/1998 | Knodel et al. |
| 5,890,642 | A | 4/1999 | Sato |
| 5,941,890 | A | 8/1999 | Voegele et al. |
| 5,947,363 | A | 9/1999 | Bolduc et al. |
| 5,947,999 | A | 9/1999 | Groiso |
| 5,951,576 | A | 9/1999 | Wakabayashi |
| 5,972,023 | A | 10/1999 | Tanner et al. |
| 5,993,476 | A | 11/1999 | Groiso |
| 6,001,110 | A | 12/1999 | Adams |
| 6,083,242 | A | 7/2000 | Cook |
| 6,306,150 | B1 | 10/2001 | Levinson |
| 2002/0029044 | A1 | 3/2002 | Monassevitch et al. |

FOREIGN PATENT DOCUMENTS

| | | |
|---|---|---|
| FR | 716780 | 12/1931 |
| FR | 2603794 A1 | 9/1986 |
| IT | 529968 | 12/1957 |
| WO | WO 9518572 A | 7/1995 |

* cited by examiner

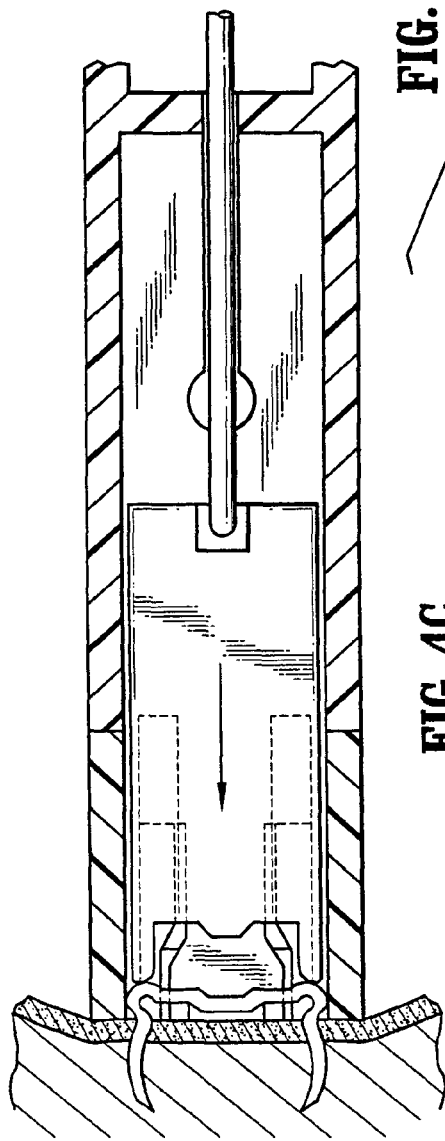
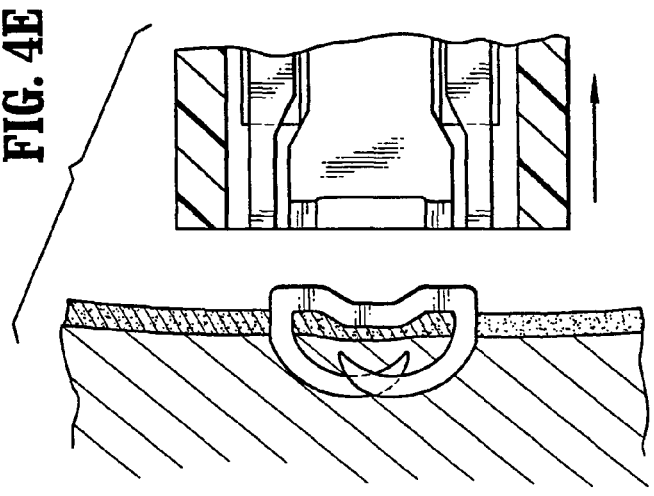
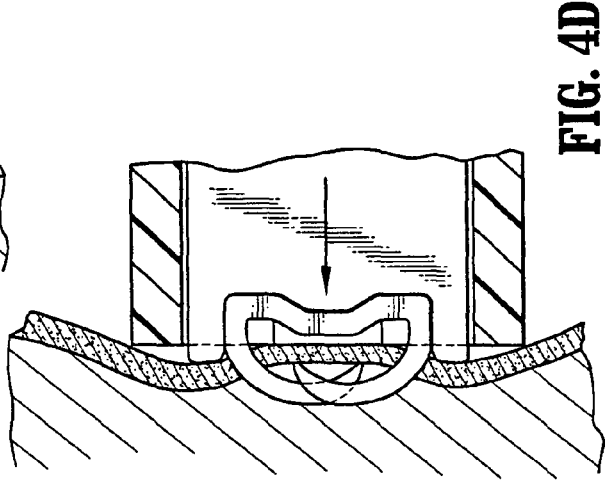
FIG. 4C
FIG. 4D
FIG. 4E

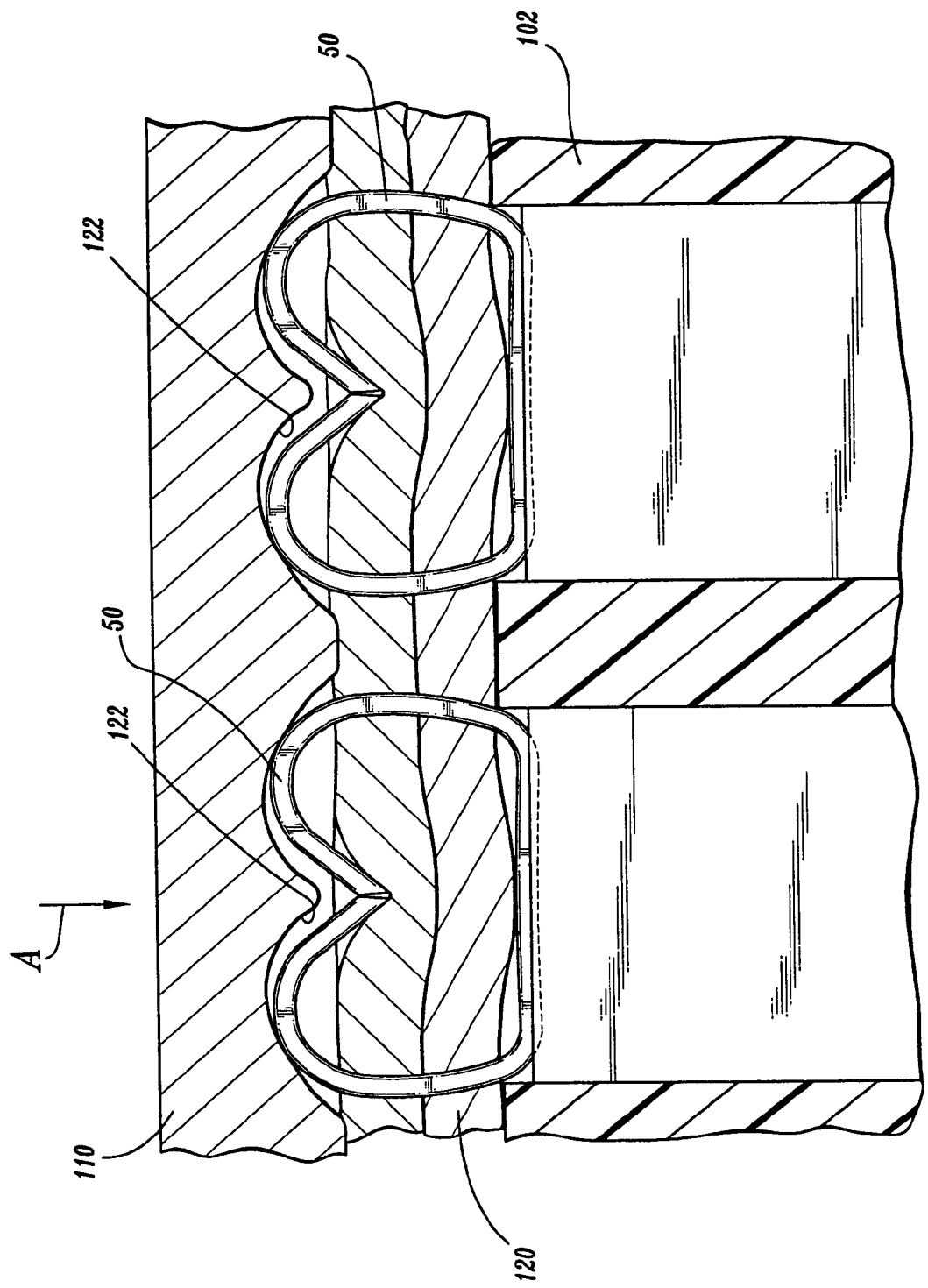

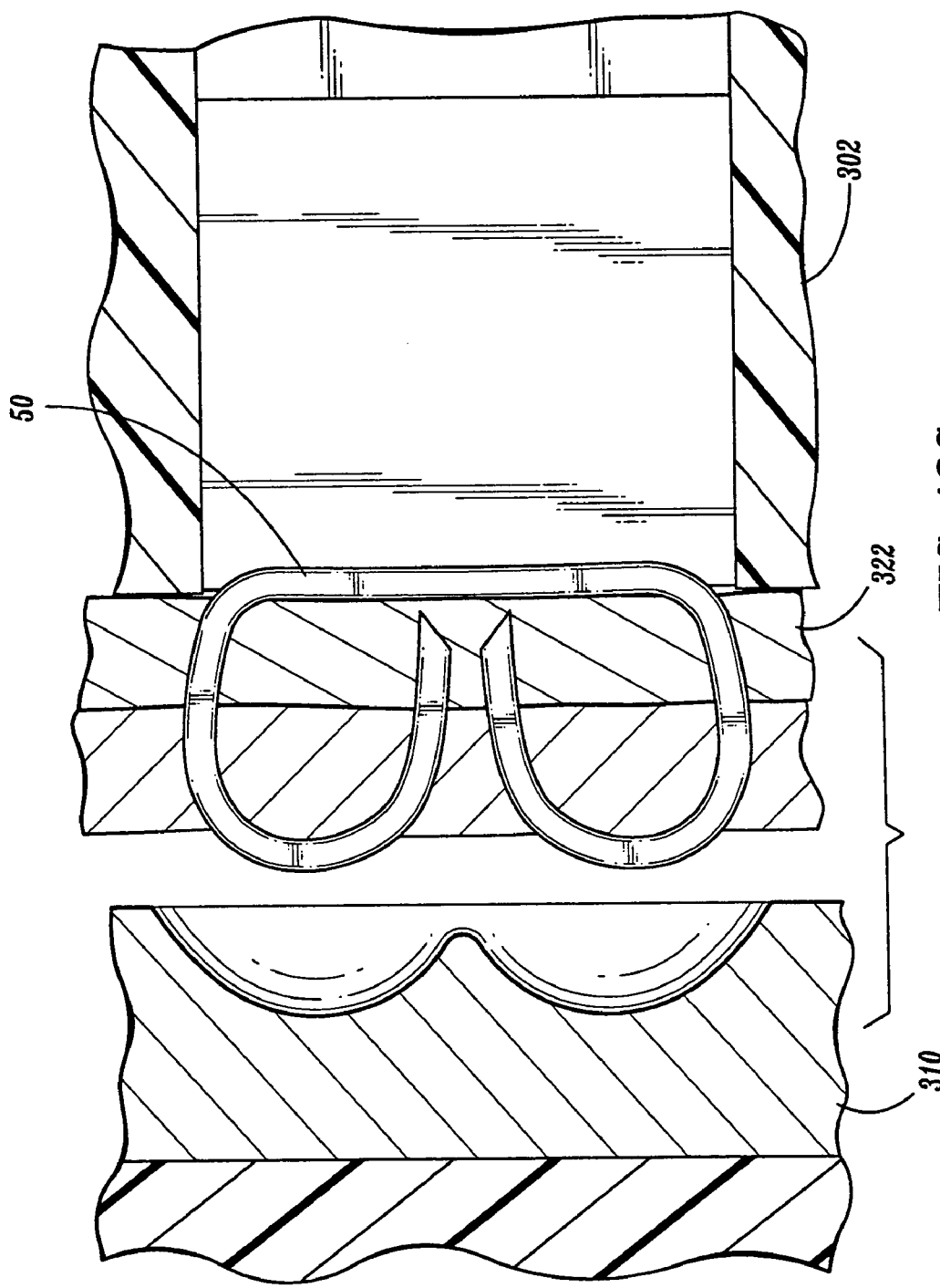

DIRECTIONALLY BIASED STAPLES AND CARTRIDGE HAVING DIRECTIONALLY BIASED STAPLES

CROSS REFERENCE TO RELATED APPLICATIONS

This application is a continuation of U.S. patent application Ser. No. 09/693,379 filed Oct. 20, 2000 now abandoned, the entire contents of which are incorporated herein by reference.

BACKGROUND

1. Technical Field

This invention relates to formable surgical fasteners and, more particularly, to directionally biased formable staples for use in surgical staplers having anvil pockets for forming the staples.

2. Background of Related Art

Surgical stapling instruments have become critical to many life saving surgical procedures. Surgical staples are usually mechanically inserted into tissue with surgical stapling instruments such as those known as anastomosis devices, including gastrointestinal anastomosis devices and transverse anastomosis devices. In such devices, the staples are loaded in one or more elongated rows into a cartridge. A mechanism for pushing, or driving the stapler is actuated to drive the staples through two or more sections of tissue toward a deforming anvil. At the conclusion of the driving operation, the legs of each staple are conventionally clamped or bent, by the anvil, to a closed configuration to complete the suture and join the tissue sections together. Gastrointestinal anastomosis-type devices drive and bend the staples aligned in a row sequentially in rapid sequence, while transverse anastomosis-type devices drive and bend all staples simultaneously. See, e.g. U.S. Pat. Nos. 4,520,817 and 4,383,634. Circular anastomosis-type devices simultaneously apply annular rows of staples to tissue. See, e.g. U.S. Pat. No. 4,304,236.

One type of conventional staple 20, shown in FIGS. 1-3, used with both gastrointestinal anastomosis and transverse anastomosis-type surgical stapling devices is made of stainless steel or titanium. The undeformed staple 20 (FIG. 1) is generally U-shaped and includes a back span 22 and two legs 24 depending substantially perpendicularly from the back span. Each leg 24 has a sharp chiseled end point 26 for piercing body organs or tissue. The chisel point also creates torque in the staple, allowing it to form. The staple penetrates the tissue from one side to engage an anvil spaced apart and located at an opposing side of the tissue. The staple is bent by having the legs engage and follow an anvil 25 to form a B-shaped closed staple 28 as shown in FIG. 2. In this closed configuration tissue is compressed between the legs and backspan of the staple.

Because of their substantially circular cross-section (FIG. 3), these conventional staples require approximately the same amount of force to form the staple into its final shape as is required to twist or malform it.

For example, referring back to FIG. 3, a conventional round cross section staple has a moment of inertia in the x forming dimension ($I_x$) given by the equation:

$$I_x = 1/4 \pi r^4$$

Its moment of inertia in the y twisting dimension ($I_y$) is given by the same equation $$I_y = 1/4 \pi r^4$$

Using a round wire stock of uniform 0.009 in diameter (r=0.0045), $$I_x = I_y = \frac{1}{4}\pi(.0045)^4$$
$$= 3.22 \times 10^{-10} \text{ in}^4$$

The Moment of Inertia Ratio, given by the equation:

is $I_y/I_x$ $$\frac{3.22 \times 10^{-10} \text{ in}^4}{3.22 \times 10^{-10} \text{ in}^4} = 1$$

In order to insure accurate and consistent formation of these conventional staples, considerable research and development has been conducted in the areas of forming and driving structures. For example, anvils have been developed with specific coatings and/or structure, see, e.g. U.S. Pat. Nos. 5,173,133 and 5,480,089. Also, staple cartridges have been configured with driver structure to balance forces encountered during staple formation. See, commonly assigned U.S. Pat. No. 4,978,049 to Green. Thus, to control and insure consistent staple formation without twisting or deformation, extremely strict manufacturing tolerances have been implemented.

Other types of staples for different types of instruments are also found in the prior art. Some have non-circular cross-section. FIGS. 4, 4A and 4B illustrate by way of example a staple of this type marketed by United States Surgical of Norwalk, Conn. for use with its MULTIFIRE ENDO HERNIA and ENDO UNIVERSAL 65 staplers. The anvil in these staplers, as shown in FIGS. 4C and 4D, is adjacent the backspan of the staple as tissue is approached from only one side. Unlike the staples described above which are formed by contact of the staple legs with anvil pockets, these staple legs are bent around an anvil abutting the backspan. This staple has a side portion H with a height dimension greater than the dimension of the base portion B (i.e. 0.020 in vs. 0.015 in.).

The Moment of Inertia Ratio is given by the equation:

$$\text{Moment of Inertia Ratio} = \frac{I_y}{I_x} = \frac{\text{Moment of Inertia About Twisting Axis}}{\text{Moment of Inertia About Forming Axis}}$$

where $I_x=(1/12)bh^3$ and $I_y=(1/12)hb^3$, with h=0.020 in. and b=0.015 in.

Thus, $I_x=(1/12)(0.015)(0.020)^3=1.0\times10^{-8}$ in$^4$, and
$I_y=(1/12)(0.020)(0.015)^3=6.0\times10^{-9}$ in$^4$.

Accordingly, $$\text{Moment of Inertia Ratio} = \frac{6.01 \times 10^{-9} \text{ in}^4}{1.10 \times 10^{-8} \text{ in}^4} = .60/1 = .60$$

This staple is specifically configured to accommodate twisting during staple formation to permit the legs of the staple to cross as shown in FIG. 4E. Thus, it is engineered so the force to form the staple is slightly greater than the force to malform or twist the staple. The forming is accomplished by bending the staple legs around an anvil positioned adjacent the inner surface 32 of the backspan 34.

U.S. Pat. No. 5,366,479 describes a hernia staple with adjacent anvil having a height of 0.38 mm and a thickness of 0.51 mm. This staple is formed the same way as in FIGS. 4C and 4D. The moment of inertia ratio of this staple in accordance with the foregoing formula is as follows:

$$I_x=(1/12)(0.51)(0.38)^3=2.33\times10^{-3}$$

$$I_y=(1/12)(0.38)(0.51)^3=4.2\times10^{-3}$$

$$\text{Moment of Inertia Ratio} = \frac{4.2\times10^{-3}}{2.33\times10^{-3}} = 1.8$$

This staple for use as described would actually result in greater force to produce the desired shape. In fact, the staple legs would likely contact each other before crossing over into their crossed configuration.

Thus, it is apparent that this type of hernia staple, i.e. where the anvil is adjacent the backspan as the tissue is approached from only one side, is quite different than the staple of the present invention, e.g. the B-shaped staple, wherein the legs penetrate through the tissue to contact anvil pockets. These anvil pockets direct the staple legs to form the staple into a closed configuration. Thus staple configuration and considerations of twisting, bending and staple formation of these hernia staples are inapplicable to these considerations for anvil pocket directed staples, such as the B-shaped staples.

It would therefore be desirable to provide a staple configuration for a staple designed to penetrate tissue and contact an anvil pocket on the opposing side of tissue, which, in complement with conventional cartridge and anvil technology, enhances correct staple formation while reducing twisting/malformation caused by misalignment or unusual tissue while minimizing reliance on strict manufacturing tolerances.

SUMMARY

In accordance with the present disclosure a directionally biased staple is provided for use in surgical staplers having anvil structure spaced from the cartridge and having anvil pockets against which the staple is formed as the legs are forced into contact with the anvil. The directionally biased staple may be constructed in a wide variety of cross-sectional configurations including rectangular, elliptical, trapezoidal, etc. All of the configurations are distinguished by having a bending region requiring more force to twist or malform the staple than is required to properly form the staple. Preferably, these staples have Moment of Inertia Ratios on the order of between about 1.1 to about 3.0. The staple preferably corresponds in other respects to conventionally formed staples, i.e. having at least a pair of leg members interconnected by a crown portion wherein the leg members come into contact with and are formed by the anvil.

BRIEF DESCRIPTION OF THE DRAWINGS

Various preferred embodiments are described herein with reference to the drawings, wherein:

FIGS. 4C, 4D and 4E illustrate the staple of FIG. 4 being formed as the legs are bent by the pusher and the backspan is held against the anvil;

FIGS. 19B and 19C are enlarged views showing the staple formation by the anvil pockets of the instrument of FIG. 19A;

DETAILED DESCRIPTION OF PREFERRED EMBODIMENTS

Figure 1:
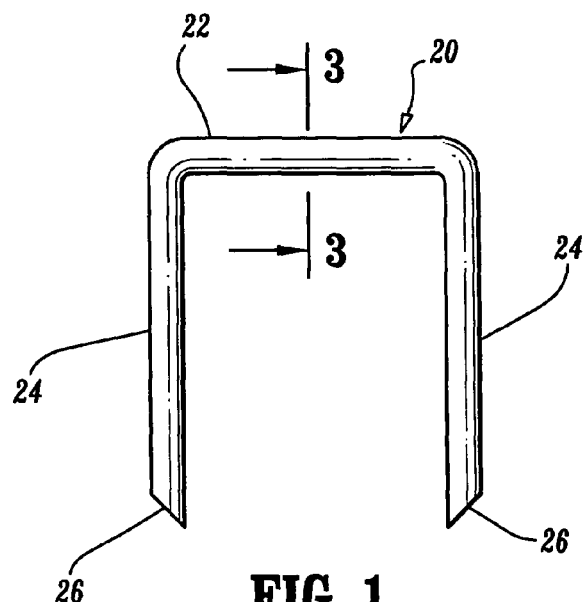
FIG. 1 is a side view of a conventional staple as known in the art.
Figure 2A:
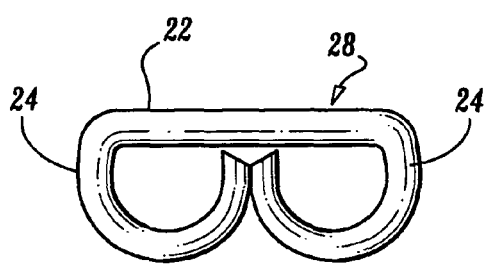
FIG. 2A is a side view of the staple of FIG. 1 formed into a "B" configuration.
Figure 3:
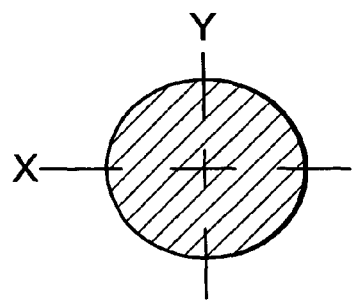
FIG. 3 is a cross-sectional view of the staple of FIG. 1 taken along line 3-3.
Figure 2B:
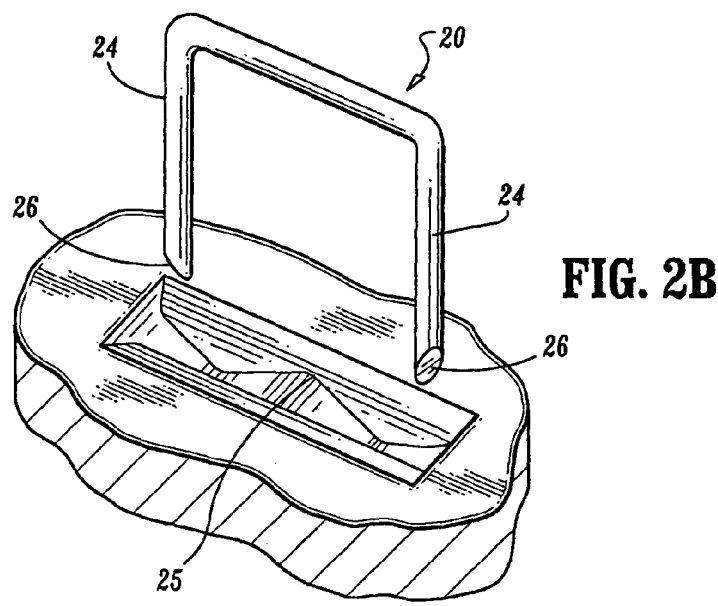
FIGS. 2B, 2C and 2D illustrate the staple of FIG. 2 being formed as the legs, after penetrating tissue, come into contact with the anvil pockets.
Figure 2C:
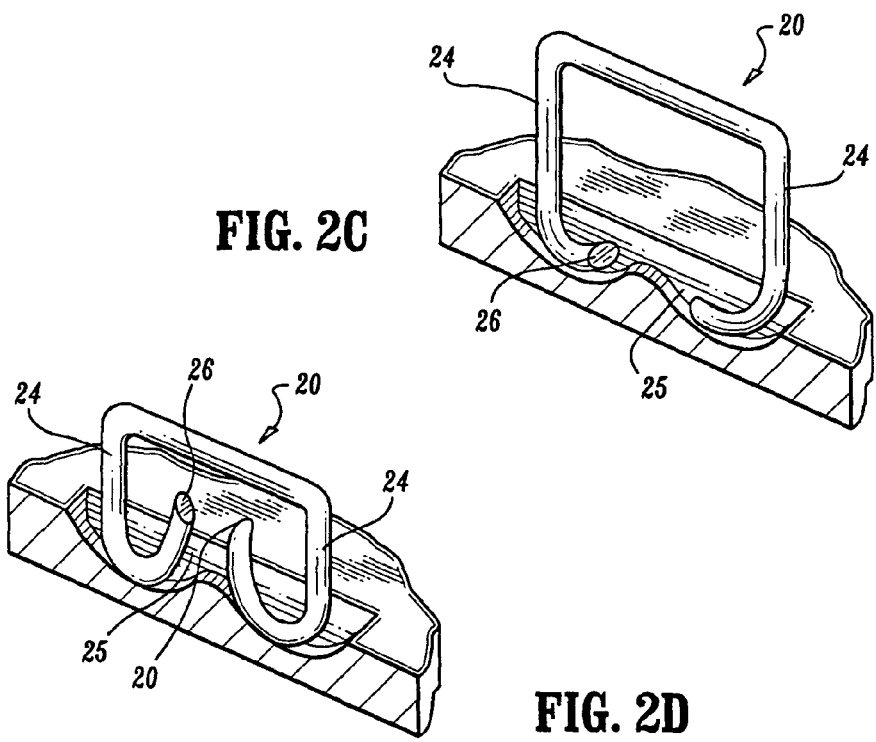
Figure 2D:
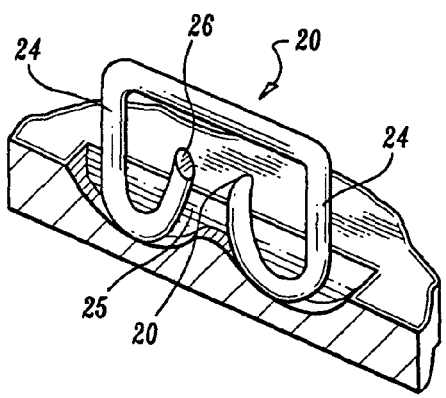
Figure 4:
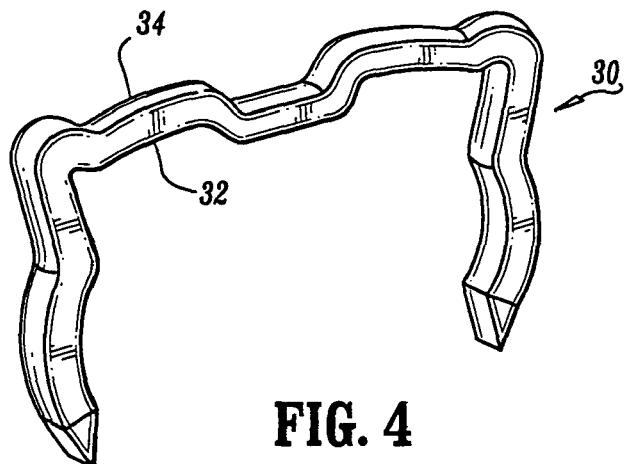
FIG. 4 is a perspective view of a conventional rectangular cross-section staple as known in the art which is formed around an anvil contacted by the backspan.
Figure 4A:
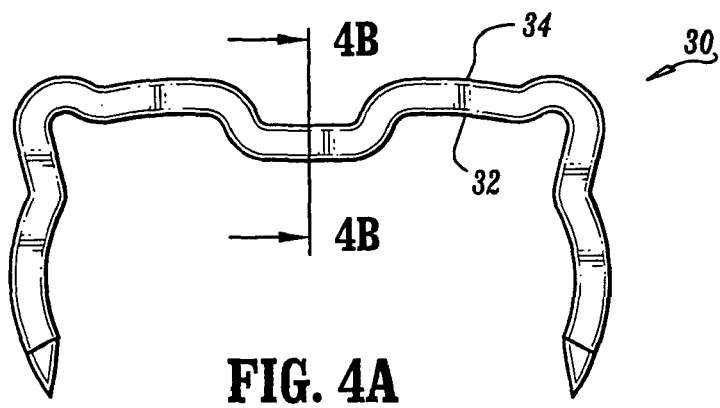
FIG. 4A is a side view of the staple of FIG. 4.
Figure 4B:
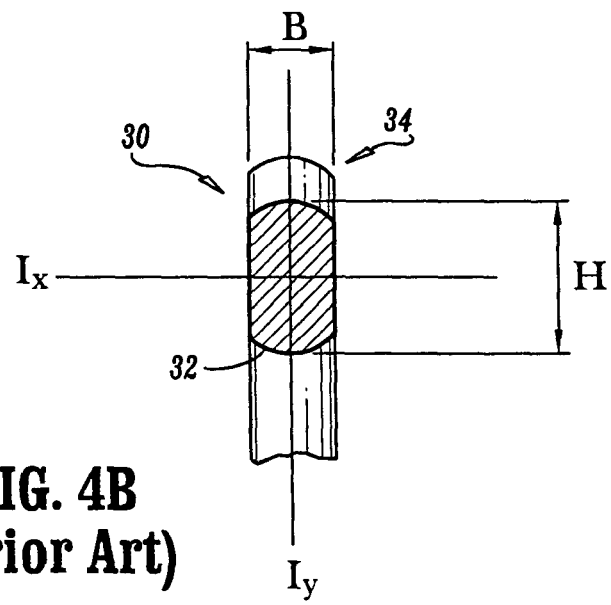
FIG. 4B is a cross-sectional view of the staple of FIG. 4 taken along line 4B-4B.

Preferred embodiments of the presently disclosed directionally biased staple will now be described in detail with reference to the drawings, in which like reference numerals designate identical or corresponding elements in each of the several views.

Figure 5:
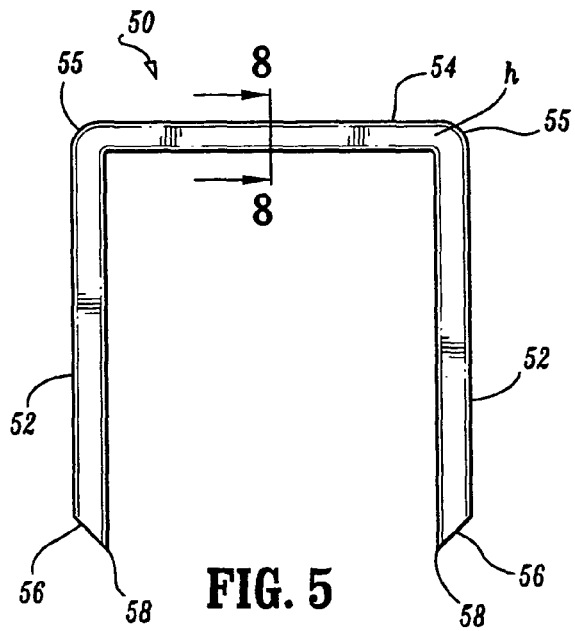
FIG. 5 is a side view of a directionally biased staple in accordance with the present disclosure.
Figure 7:
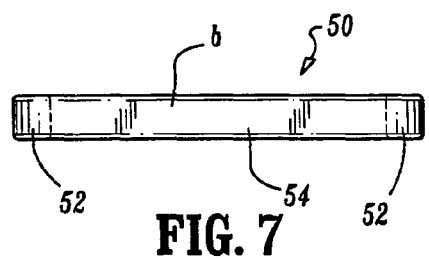
FIG. 7 is a top view of the staple of FIG. 5.
Figure 9B:
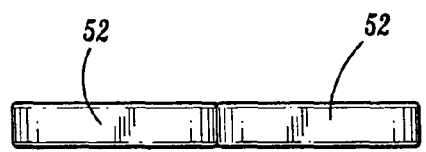
FIG. 9B is an end view showing the coplanarity of the "B" sections of the staple of FIG. 9A.
Figure 6:
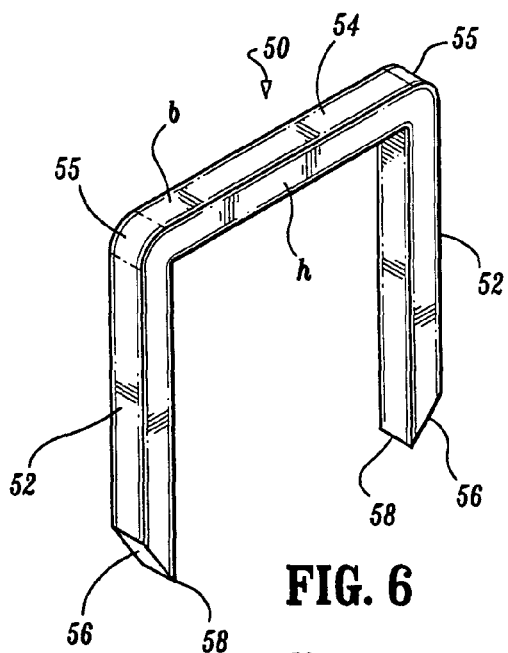
FIG. 6 is a perspective view of the staple of FIG. 5.

A directionally biased staple 50 in accordance with one embodiment of the present disclosure is illustrated in FIGS. 5-9. Referring specifically to FIGS. 5-7, staple 50 has a U-shaped configuration and includes a pair of substantially parallel legs 52 connected by a crown portion 54 with a bending region 55 therebetween. The legs are shown perpendicular to the backspan and are substantially straight along their length. Tissue penetrating portions 56 are preferably formed adjacent a distal end of legs 52. These penetrating portions 56 may be of any known configuration which facilitates entry of the legs 52 into tissue to be stapled. As shown in FIG. 5, the tissue penetrating portions 56 are preferably formed in a chisel shape with points 58 adjacent inner facing sides of legs 52.

Figure 8:
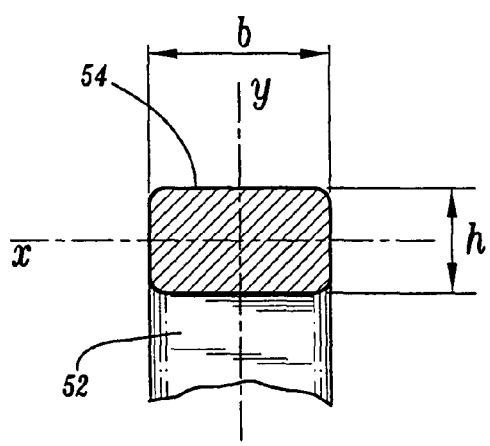
FIG. 8 is a cross-sectional view of the staple of FIG. 5 taken along line 8-8.
Figure 9A:
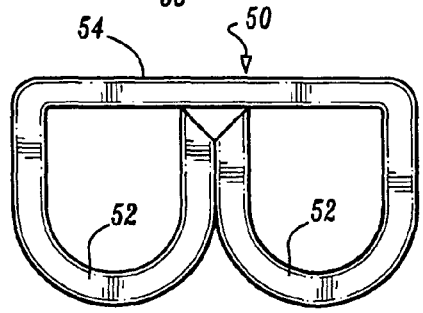
FIG. 9A is a side view of the staple of FIG. 5 after it has been deformed to a "B" configuration.
Figure 10A:
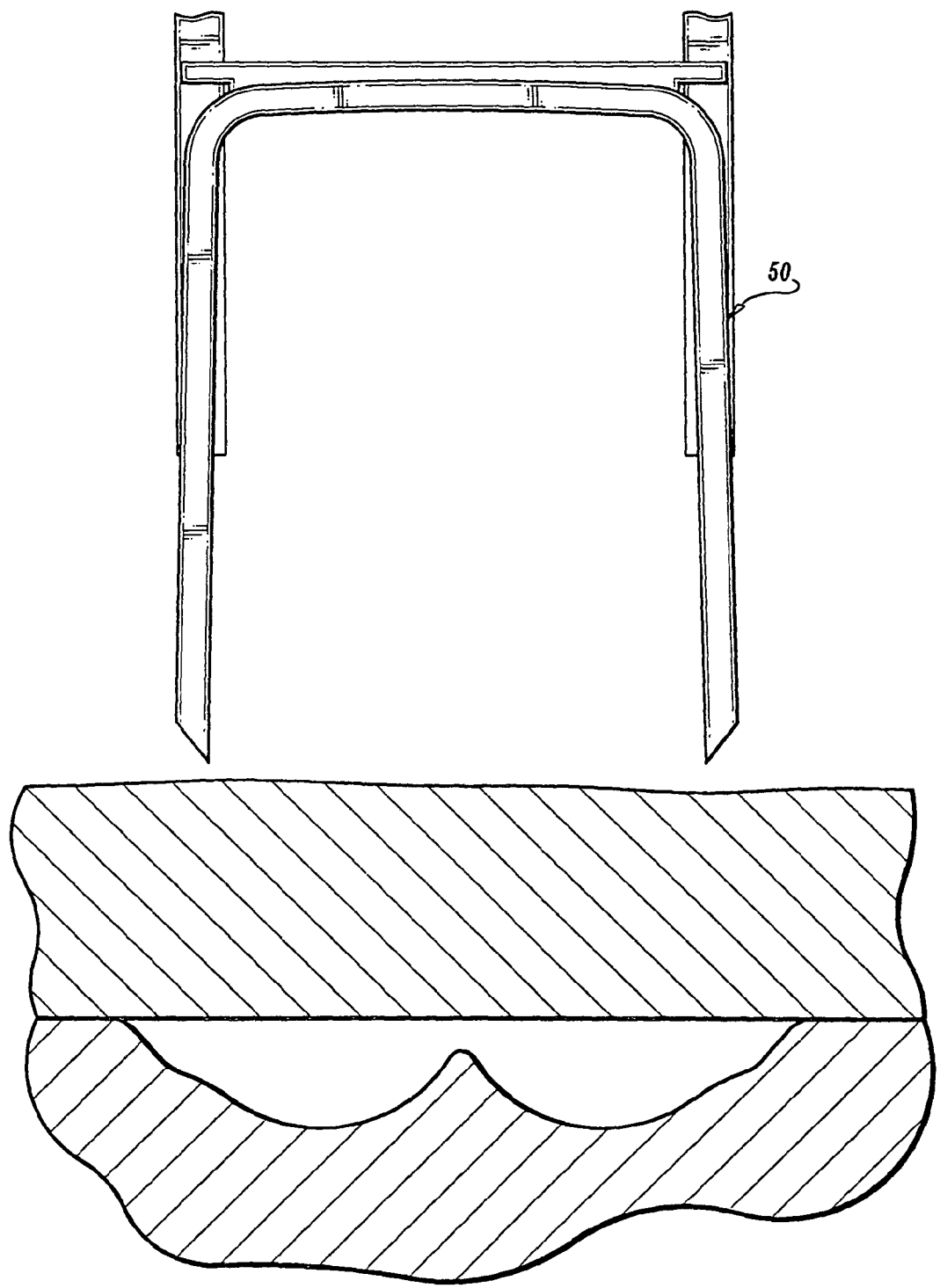
FIGS. 10A-10F are side views showing staple formation of the staple of FIG. 5 as the staple penetrates tissue and the legs come into contact with the anvil pockets.
Figure 10B:
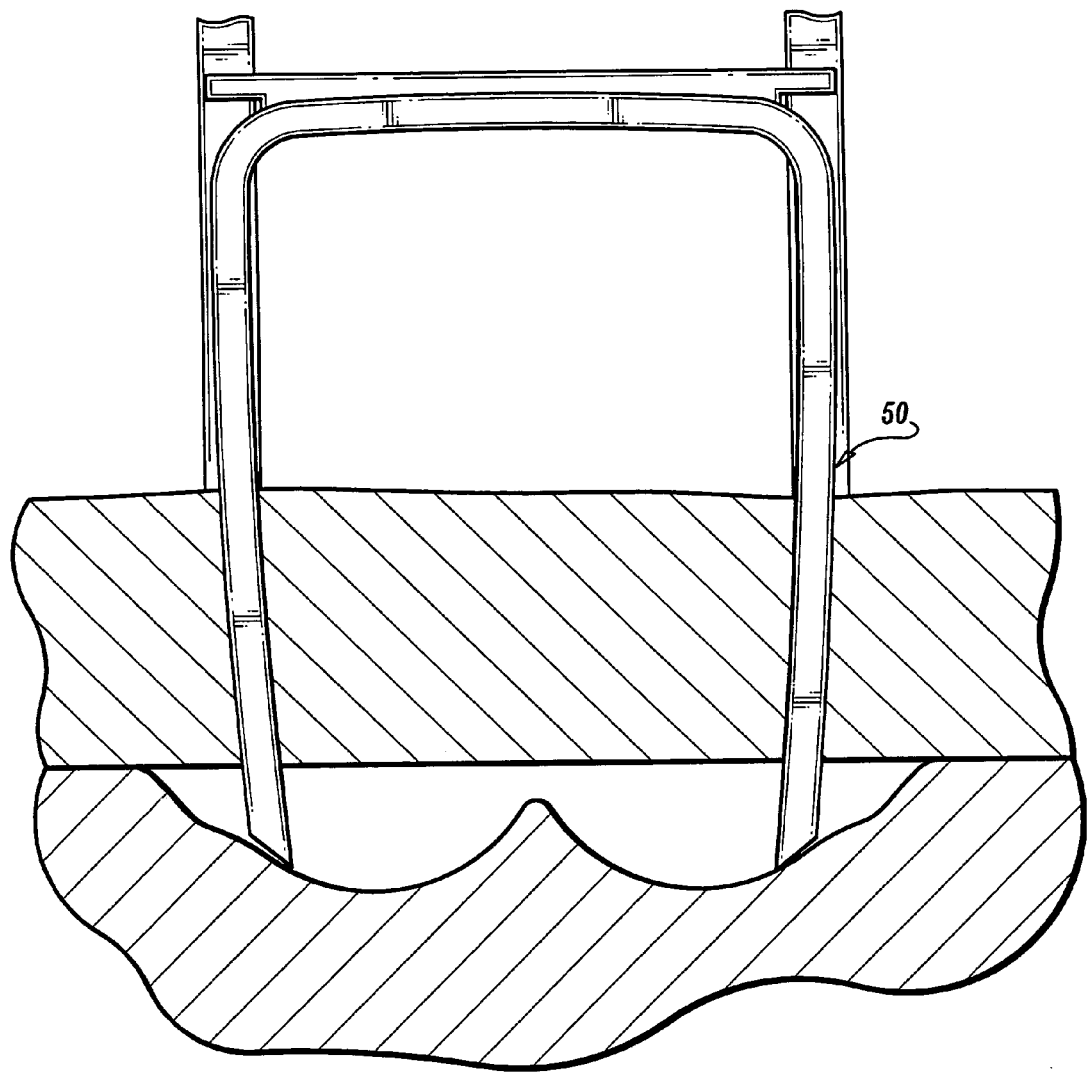
Figure 10C:
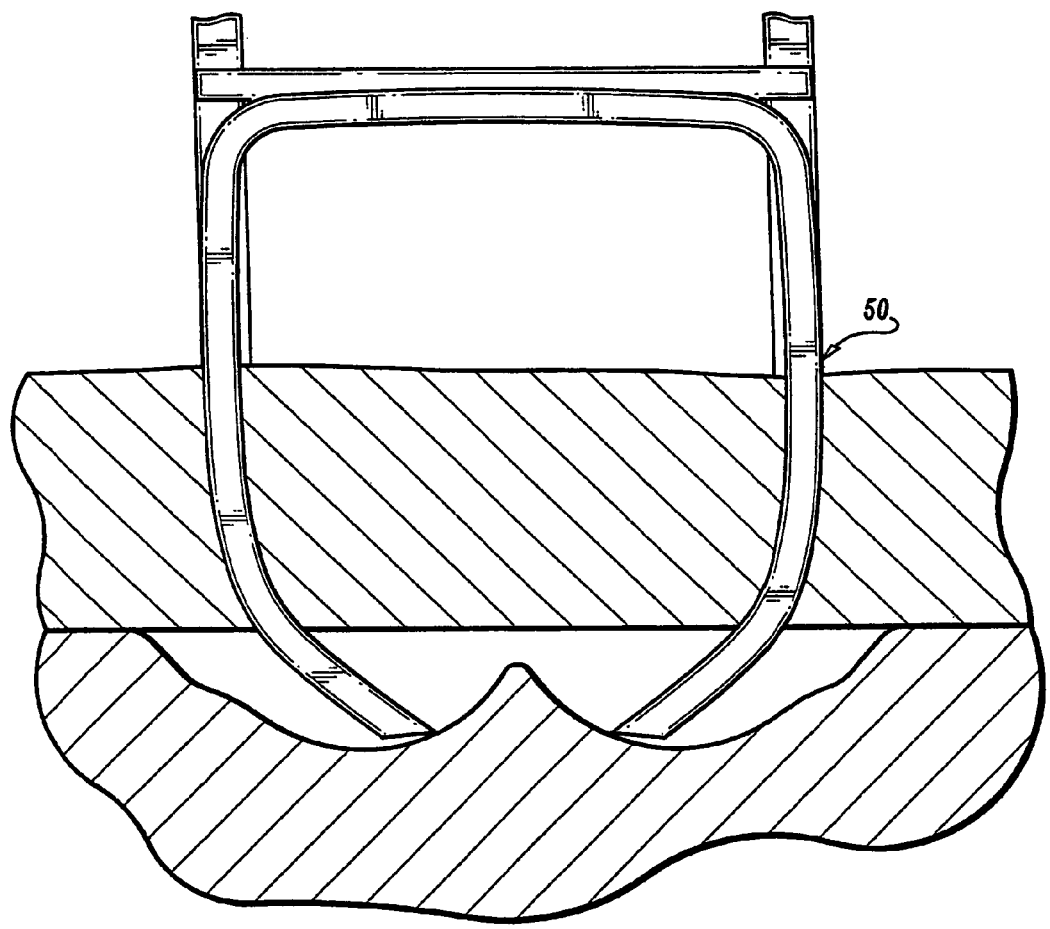
Figure 10D:
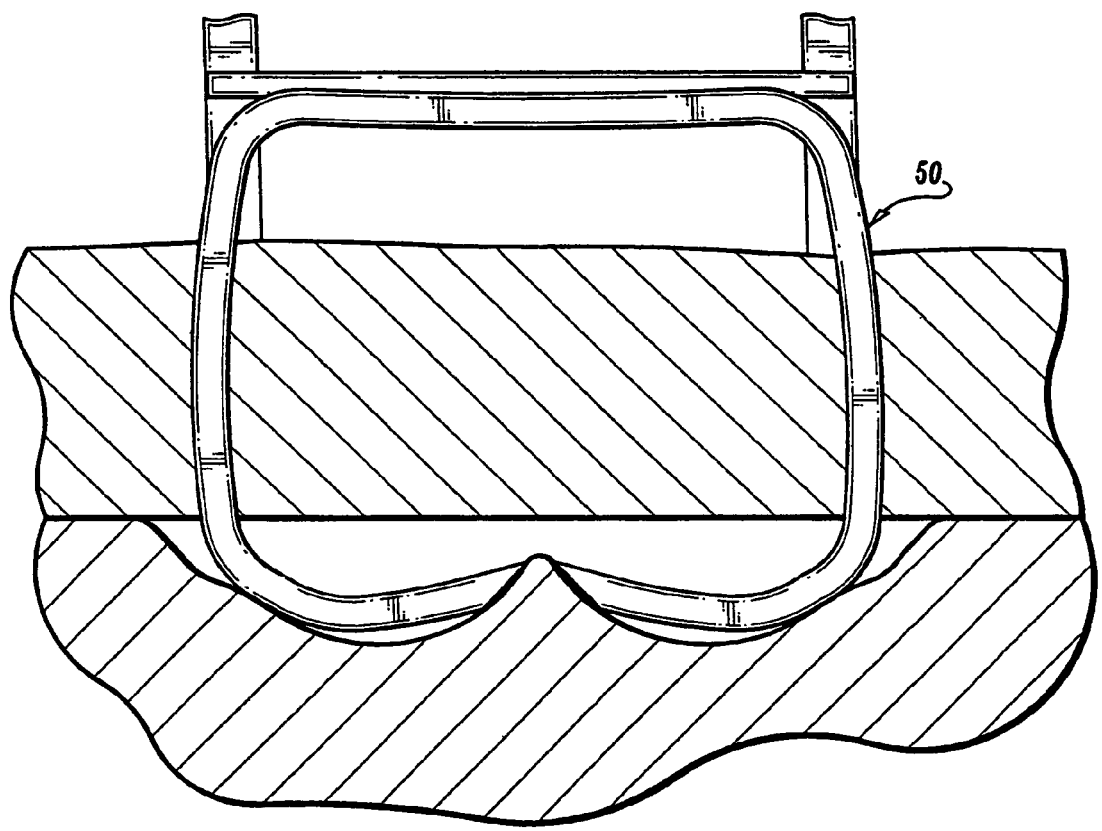
Figure 10E:
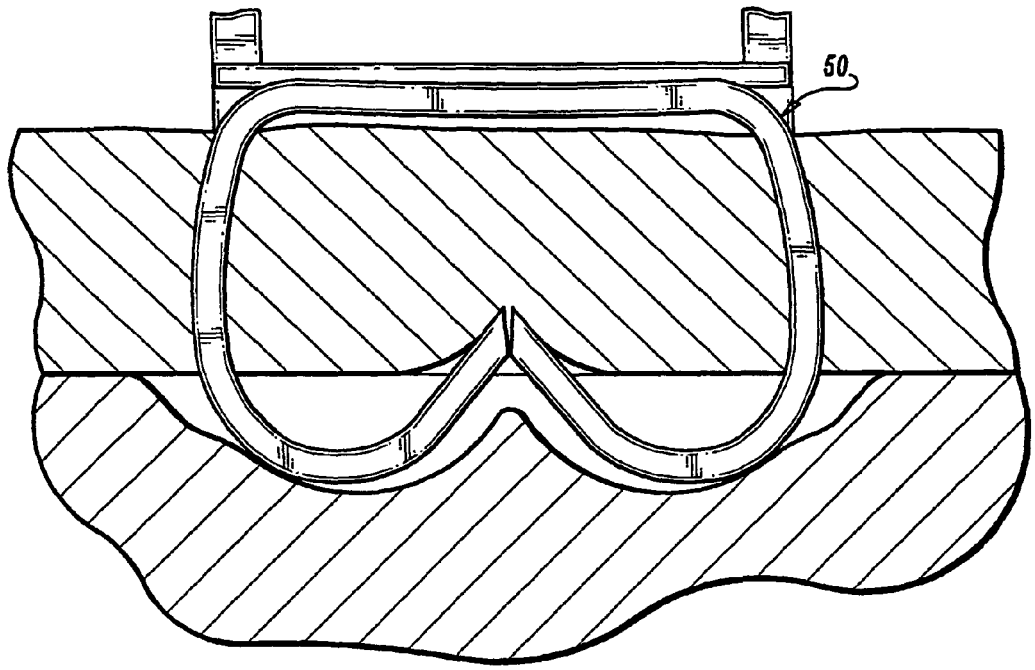
Figure 10F:
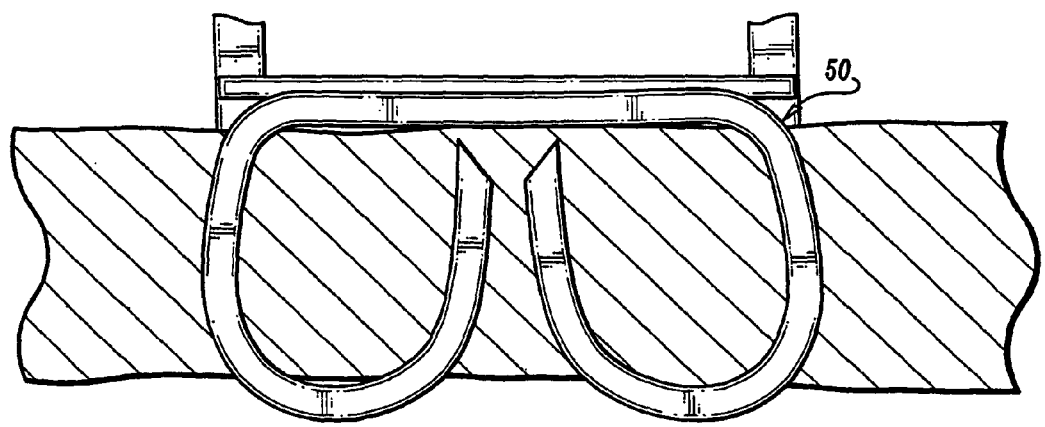

In this embodiment, the cross section is preferably formed in a substantially rectangular configuration as shown in FIG. 8 with x designating the major base dimension (b) and y designating the minor height dimension (h) of the crown portion of the staple when positioned in an inverted-U configuration as shown in FIG. 5. As used herein, the staple is intended to be formed about the x dimension (x axis). Thus, as illustrated in FIGS. 10A-10F staple 50 is formed downward relative to the page.

This cross-sectional configuration may be achieved by any known method including extrusion, rolling, coining, etc. Preferably, this configuration is accomplished by flat rolling round wire stock on opposing sides. In the fabrication process, the stock can be pre-rolled by the wire manufacturer or may be round wire stock which is rolled into the desired cross-sectional configuration by the staple manufacturer.

$I_y$ of the cross-sectional configuration of the novel staple illustrated in FIG. 5 is given by the equation:

$$I_y=(1/12)(b)^3(h)$$

For a base dimension b=0.010 in and a height dimension h=0.008 in, $$I_y=(1/12)(0.010)^3(0.008)$$

$$I_y=6.67\times10^{-10}\ in^4$$

$I_x$ is given by the equation:

$$I_x=(1/12)(b)(h)^3$$

$$I_x=(1/12)(0.010)(0.008)^3$$

$$I_x=4.26\times10^{-10}\ in^4$$

The Moment of Inertia ratio ($I_y/I_x$) is thus $$\frac{6.67\times10^{-10}\ in^4}{4.26\times10^{-10}\ in^4}=1.57$$

Similarly, for a base dimension b=0.012 in and a height dimension h=0.008 in, $I_x=1.0\times10^{-9}\ in^4$ and $I_y=5.12\times10^{-10}\ in^4$, yielding a Moment of Inertia ratio of 1.95.

Given that $I_y$ defines the dimension corresponding to proper formation of the staple when fired and $I_x$ defines the dimension corresponding to twisting and/or malformation, it is readily apparent that the directionally biased configurations provide a "functionally similar" forming force as a conventional round staple while requiring up to twice as much force to twist or malform when compared to conventional staples. This novel staple provides a substantial improvement over conventional staples.

Table 1 below sets forth by way of example Moment of Inertia Ratios for a variety of sizes and types of novel directionally biased staples for use in surgical staplers. Clearly staples of other dimensions are contemplated so long as they have the novel moment of inertia ratio described herein.

| Staple Size | Height (in.) | Base (in.) | $I_y$ | $I_x$ | $I_y/I_x$ Moment of Inertia Ratio |
|---|---|---|---|---|---|
| 3.5 mm. Titanim | .007 | .010 | 5.83 × 10⁻¹⁰ | 2.86 × 10⁻¹⁰ | ≈2.04/1 |
| 3.5 mm. Stainless Steel | .007 | .0115 | 8.87 × 10⁻¹⁰ | 3.29 × 10⁻¹⁰ | ≈2.70/1 |
| 3.8 mm. Stainless Steel | .007 | .010 | 5.83 × 10⁻¹⁰ | 2.86 × 10⁻¹⁰ | ≈2.04/1 |
| 4.8 mm. Titanim | .009 | .014 | 2.00 × 10⁻⁹ | 8.51 × 10⁻¹⁰ | ≈2.35/1 |
| 4.8 mm. Titanim | .007 | .0115 | 8.87 × 10⁻¹⁰ | 3.29 × 10⁻¹⁰ | ≈2.70/1 |

Further, as illustrated below, for comparable size staples, the novel staple configuration provides increased resistance to twist without changing firing forces.

For example, twisting stress $\sigma_b$ is defined by the equation:

$$\sigma_b = \frac{Mc}{Iy}$$

with moment M kept constant at M=1 lb·in.

For a conventional round 0.009 in. diameter staple: M=1 lb·in; c=0.0045 in; and $I_x=I_y=3.22\times10^{-10}$ in$^4$, so $$\sigma_b = \frac{(1.0\ \text{lb in})(.0045\ \text{in})}{3.22\times10^{-10}\ \text{in}^4}$$

$$\sigma_b = 13,975\ \text{ksi}$$

For the directionally biased staple of FIG. 8 having b=0.010 in and h=0.008 in: M=1.0 lb·in; c=0.005 in; and $I_y=6.67\times10^{-10}$ in$^4$.

$$\sigma_b = \frac{(1.0\ \text{lb in})(.005\ \text{in})}{6.67\times10^{-10}\ \text{in}^4}$$

$$\sigma_b = 7,496\ \text{ksi}$$

Thus, not only is this embodiment of the novel staple more resistant to twisting and/or malformation, e.g.≈14,000 ksi for the conventional staple vs.≈7,500 ksi for the novel staple, it also maintains minimal firing forces. The directionally biased staple is effectively desensitized against the effects of misalignment during staple formation while, at the same time maintaining a minimal firing force. This directionally intelligent design can reduce malformations caused by misalignment or twisting as well as reduce the need for very sensitive manufacturing tolerances for anvils and anvil forming cups, cartridges, etc.

Figure 11A:
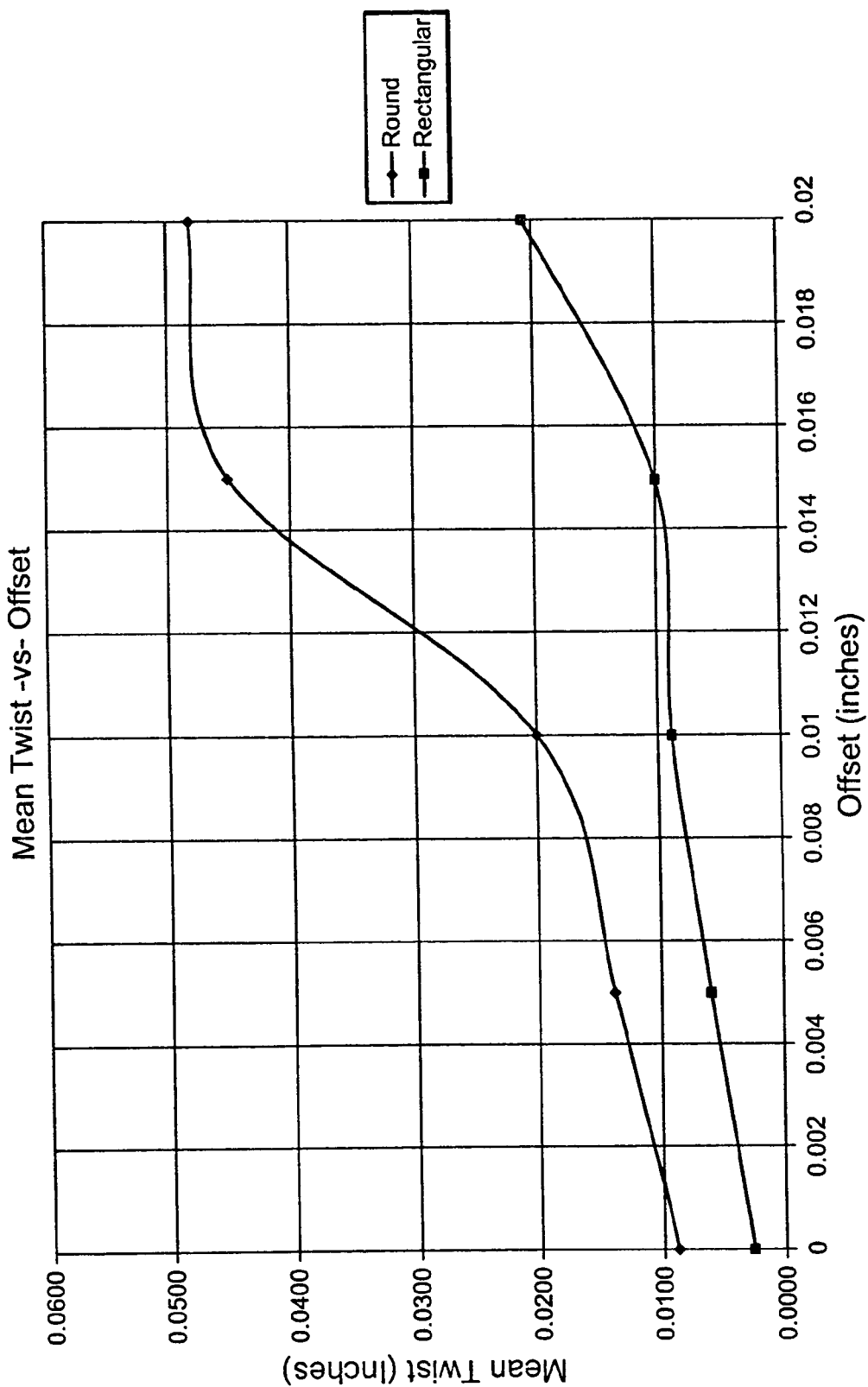
FIG. 11A graphically illustrates the comparison of the mean twist (in inches) vs the offset of the conventional staple of FIG. 1 and the novel staple of FIG. 5.
Figure 11B:
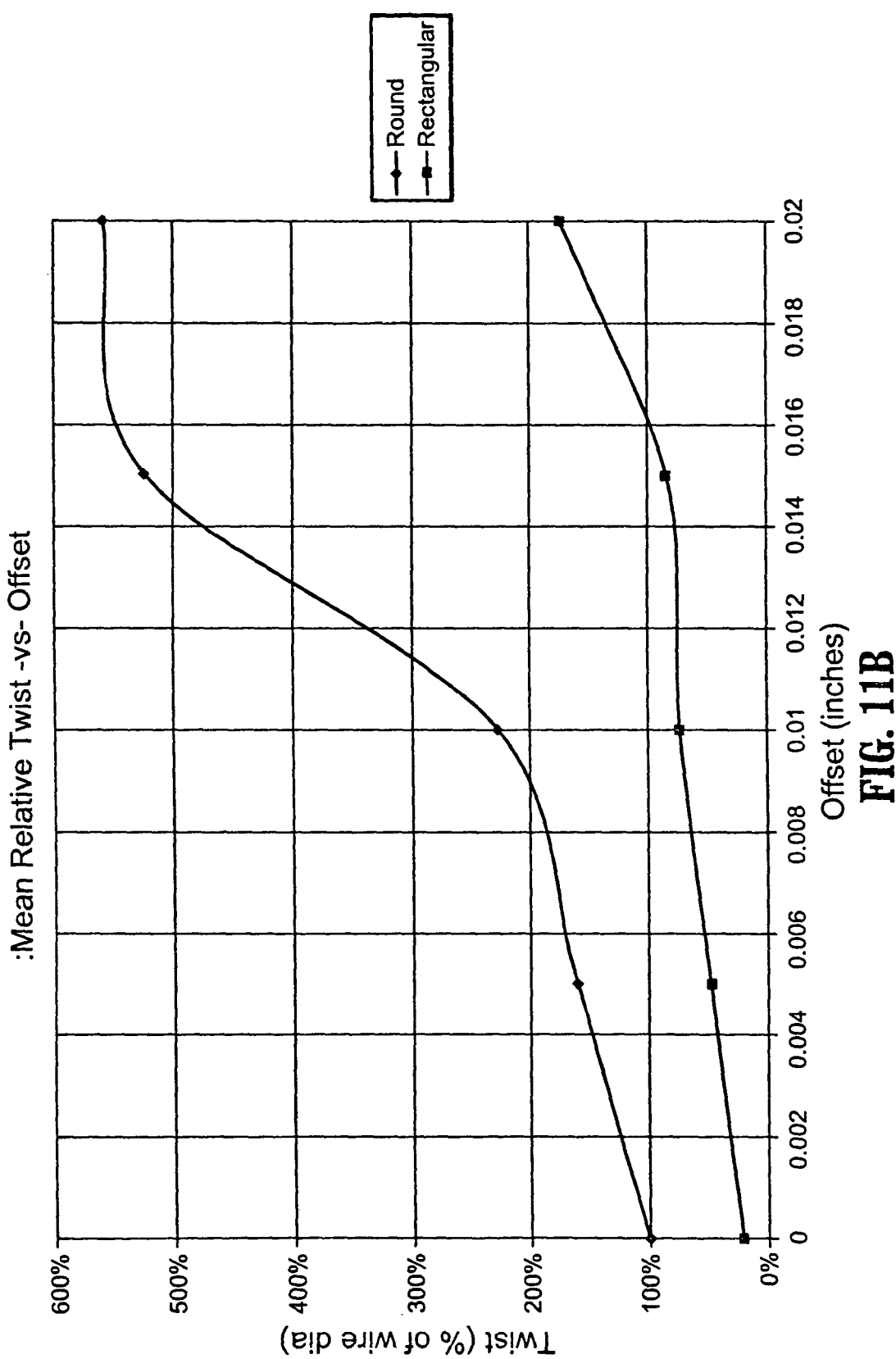
FIG. 11B graphically illustrates the comparison of the mean twist (in %) vs the offset of the conventional staple of FIG. 1 and the novel staple of FIG. 5.

The benefits of the novel staple can also be appreciated by reference to the graphs of FIGS. 11A and 11B. Since staples are forced through thick tissue and the staple cartridge and anvil can flex as tissue is compressed and can move slightly relative to another, this affects the point of contact between the staple leg points and the anvil. For example, if the anvil moves slightly out of alignment, the staple legs will contact a different point of the anvil which can affect uniform formation of the staple. Additionally, due to manufacturing tolerances, the staple points may not contact the anvil in the exact optimal location. Although such staple formation is clinically satisfactory and effective, the novel staple of the present application provides for more uniform formation of the row of staples and accommodates for manufacturing tolerances as it is more resistant to twisting. That is, the staple will have the tendency to bend in the direction of the thinner dimension which is desired since in this case the thinner dimension defines the desired bending direction. By relaxing manufacturing tolerances, the cost of manufacturing is reduced as well.

As shown in FIG. 11A, the prior art round staple, since the height and width are the same, can twist in different directions if there is misalignment between the staple and anvil. Thus the direction of twisting cannot be controlled. In contrast, the Moment of Inertia ratio of the novel staple of the present invention results in reduced twisting. Note that not only is there more twisting initially with the prior art staple, but as the offset increases, the amount of twisting in the current staple is greater at any degree of offset. The percentage of twist is defined as x/d×100% wherein x is the distance between the centerline of the staple and d is the diameter (or width) of the staple.

Figure 12A:
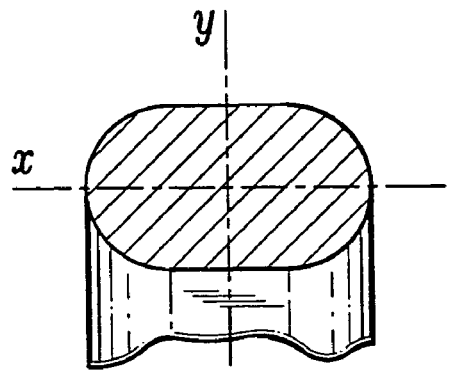
FIG. 12A is a cross-sectional view of another embodiment of a directionally biased staple in accordance with the present disclosure.
Figure 12C:
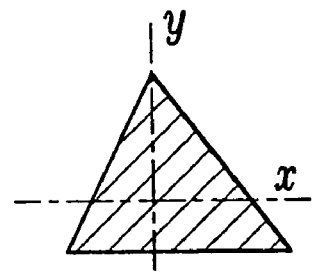
FIG. 12C is a cross-sectional view of another embodiment of a directionally biased staple in accordance with the present disclosure.
Figure 12B:
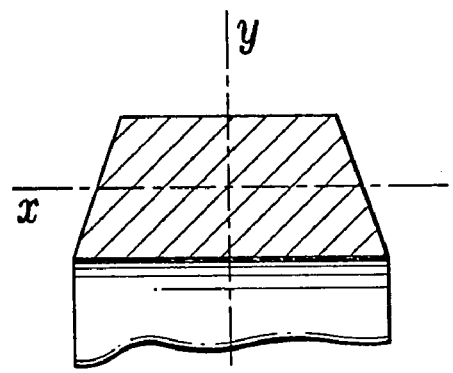
FIG. 12B is a cross-sectional view of another embodiment of a directionally biased staple in accordance with the present disclosure.
Figure 13:
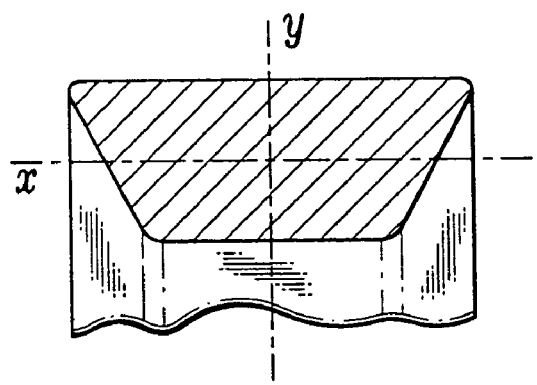
FIG. 13 is a cross-sectional view of another embodiment of a directionally biased staple in accordance with the present disclosure.
Figure 14:
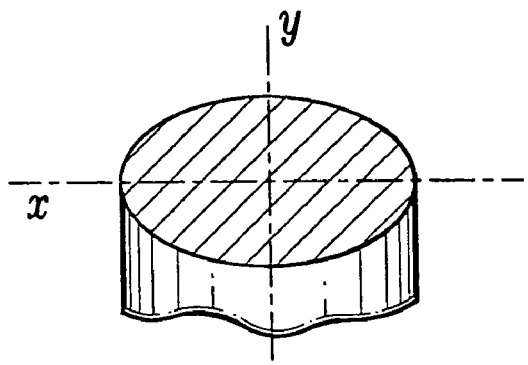
FIG. 14 is a cross-sectional view of another embodiment of a directionally biased staple in accordance with the present disclosure.

FIGS. 12-14 illustrate alternate directionally biased cross-sectional configurations in accordance with the disclosure. These cross-sectional configurations all have aspect ratios in the range of about 1.1 to about 3.0 wherein the x axis designates the major base dimension (b) and the y-axis designates the minor height dimension (h) in each of these cross-sections.

FIGS. 15-19 disclose by way of example several types of surgical staplers which can utilize the novel directionally biased staples. Other types of surgical staplers are also contemplated.

Figure 15:
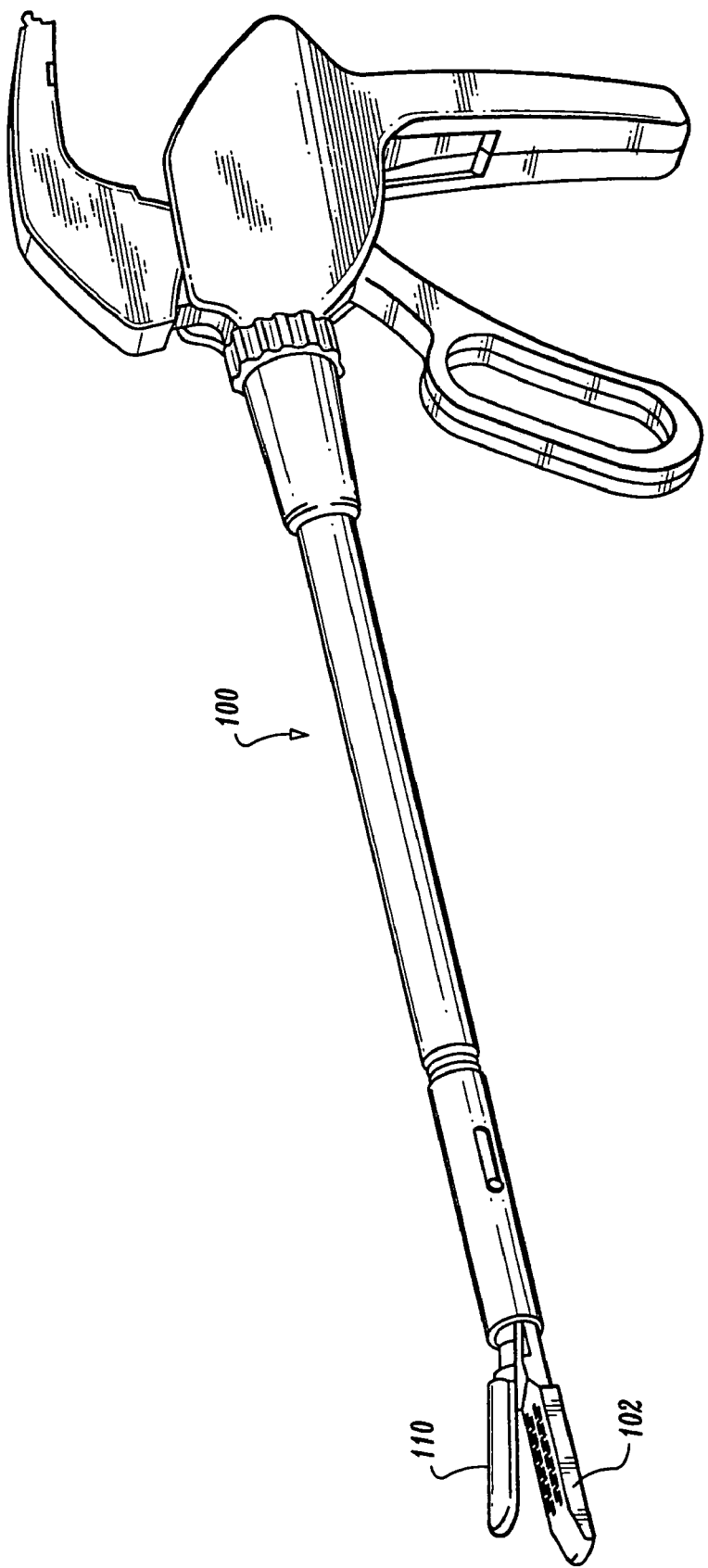
FIG. 15 is a perspective view of an endoscopic gastrointestinal anastomosis-type device for firing the staple of FIG. 5.
Figure 16:
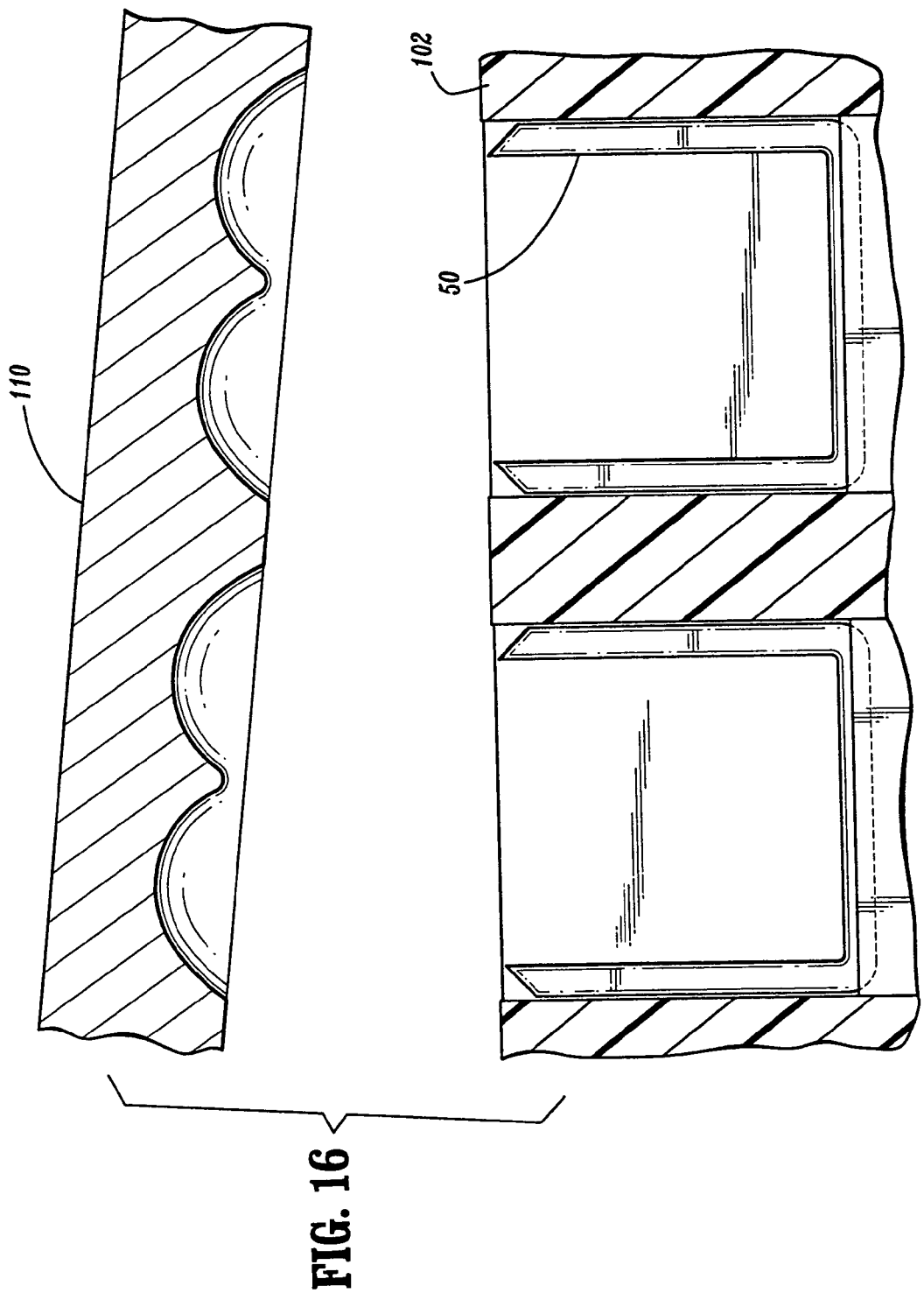
FIGS. 16-16C are enlarged views showing the staple formation by the anvil pockets of the instrument of FIG. 15.
Figure 16A:
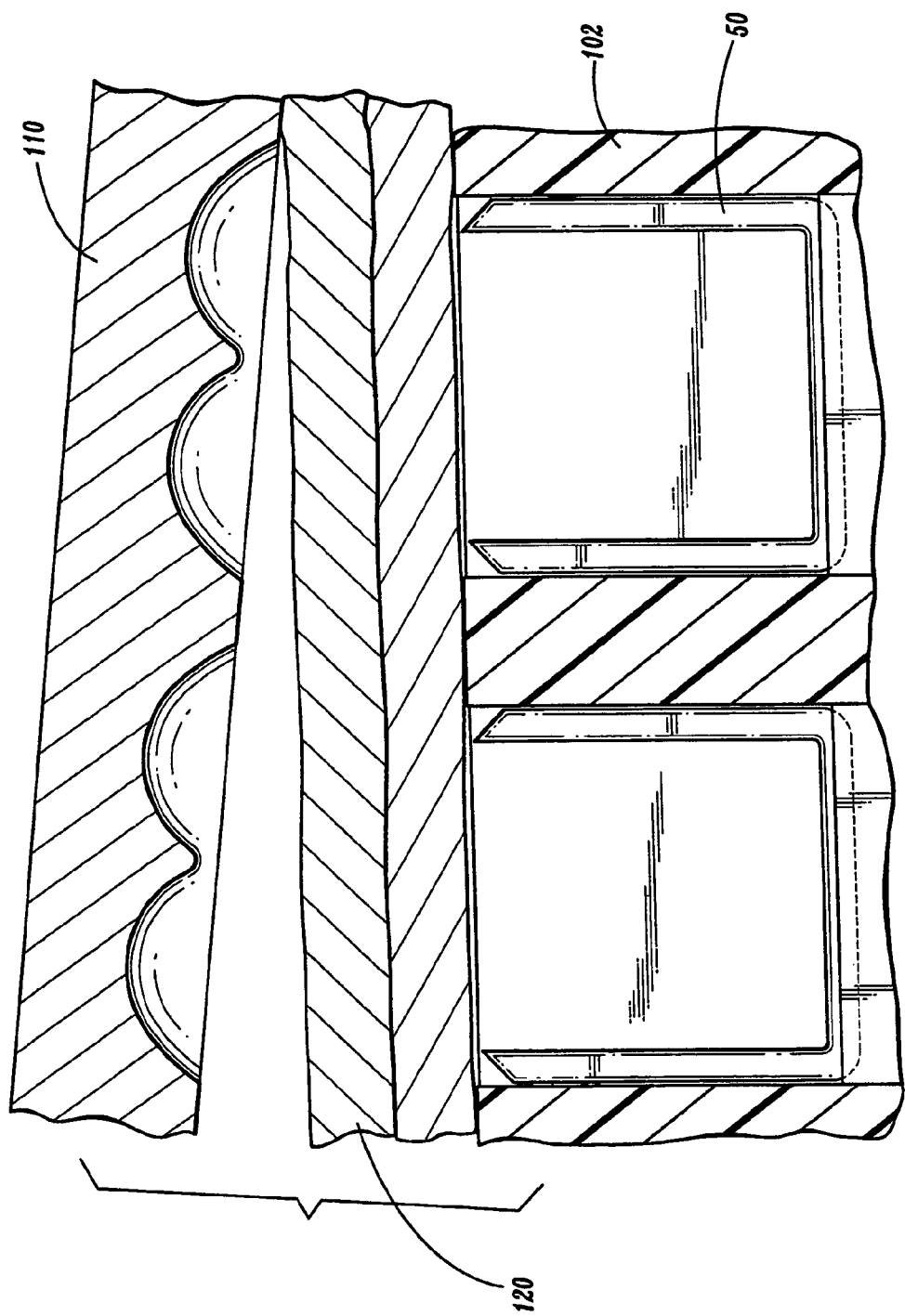
Figure 16C:
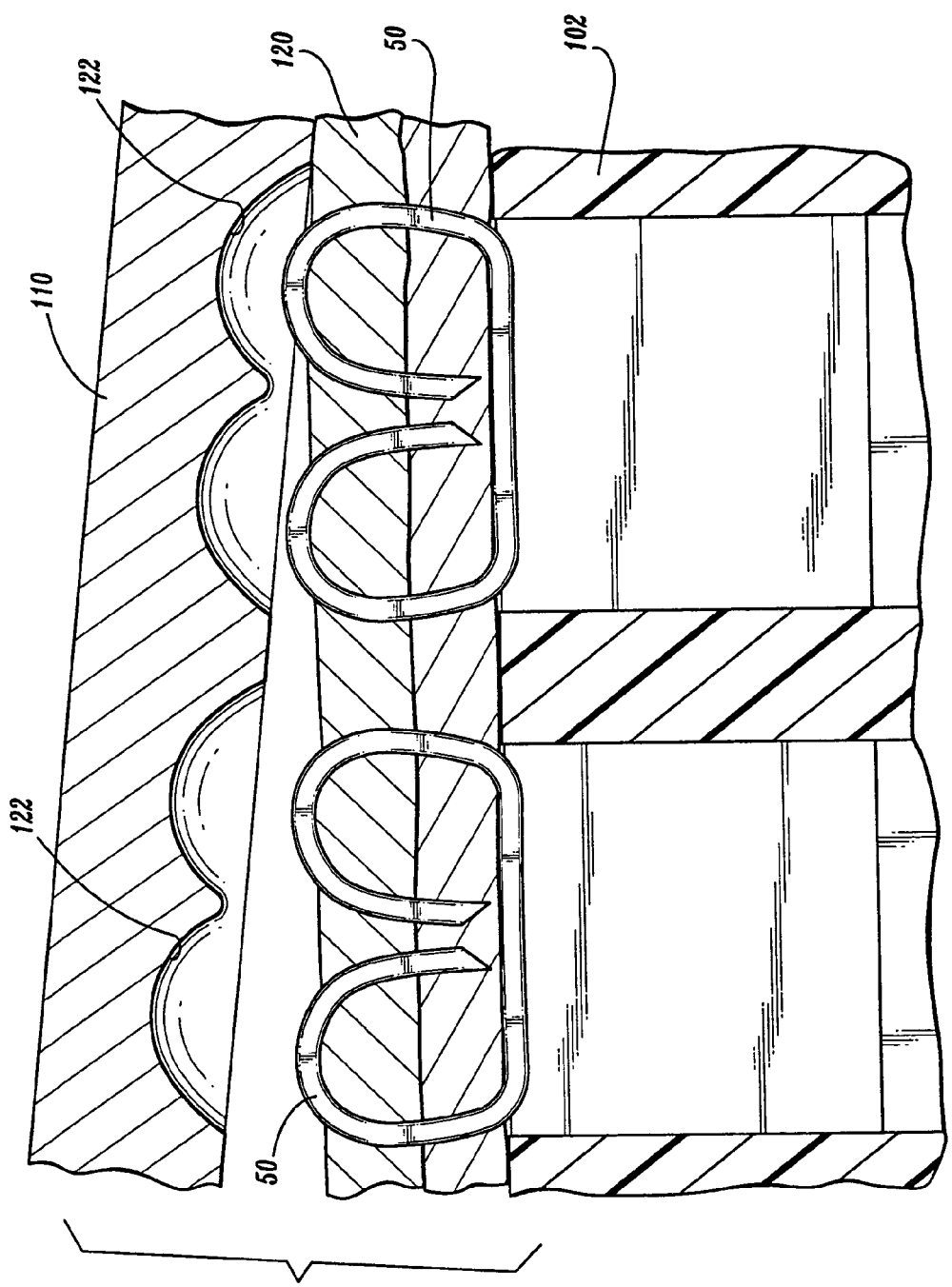

FIG. 15 illustrates a known endoscopic sequential stapler 100 including an anvil 110 and a staple cartridge 102 having novel directionally biased staples 50 loaded into the staple cartridge 102 thereof Referring to FIGS. 16-16C, with anvil 110 and staple cartridge 102 in an open position (FIG. 16), tissue 120 is positioned between anvil 110 and cartridge 102 (FIG. 16A). Anvil 110 is now pivoted in the direction indicated by arrow "A" towards cartridge 102 (FIG. 16B) in a known manner to compress tissue 120 between anvil 110 and staple cartridge 102. Thereafter, staples 50 are ejected from staple cartridge 102 into pockets 122 formed on anvil 110. Pockets 122 deform staples 50 into a substantially B-shaped configuration (FIG. 16C). Anvil 110 can now be pivoted to the open position to permit tissue 120 to be removed from stapler 100.

Figure 17:
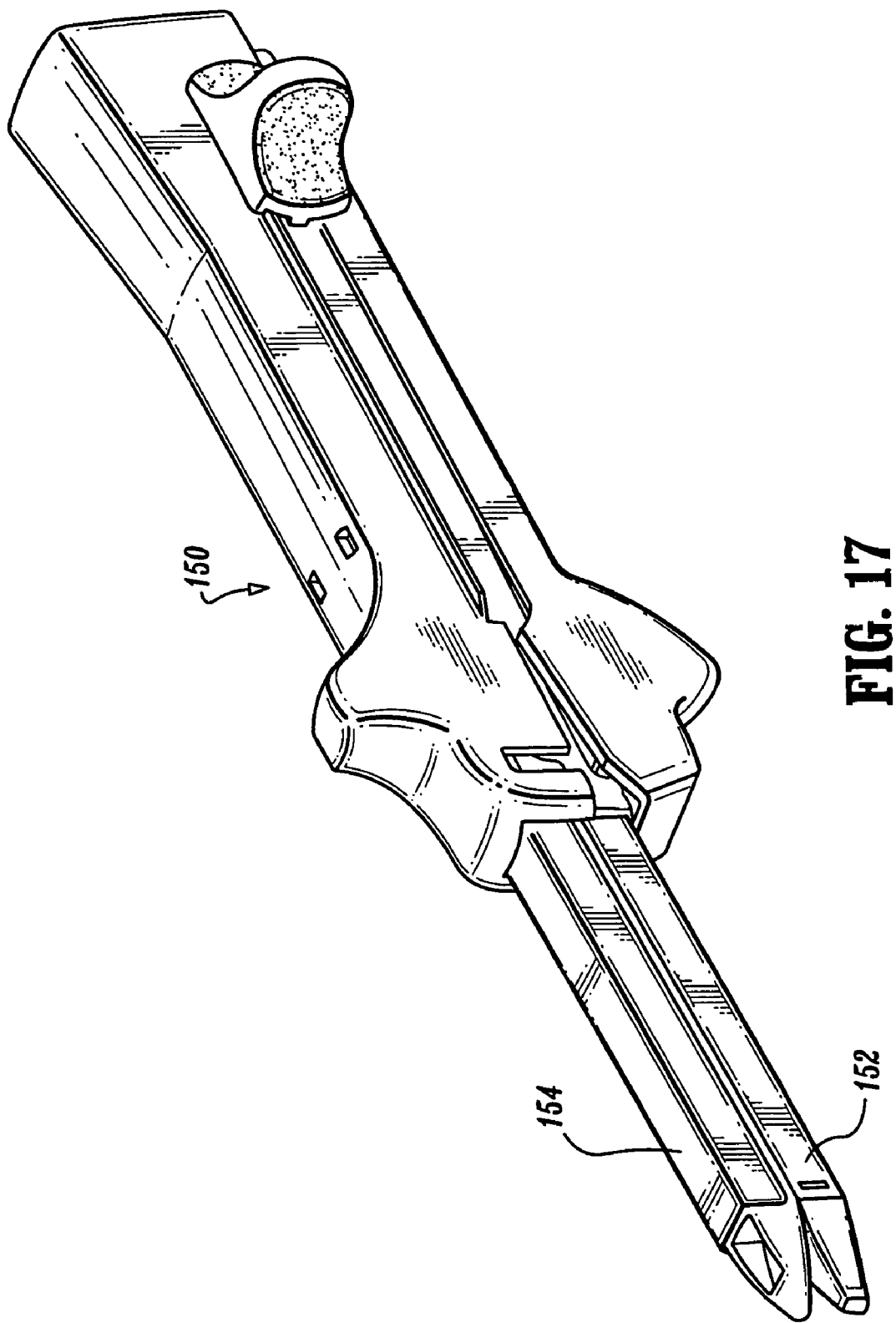
FIG. 17 is a perspective view of a gastrointestinal anastomosis-type device for firing the staple of FIG. 5.

FIG. 17 illustrates a known open type sequential stapler 150 including an anvil 152 and a staple cartridge 154 having novel directionally biased staples loaded therein. Ejection of staples from stapler occurs in a manner similar to that disclosed in FIGS. 16-16C and will not be discussed in further detail herein.

Figure 18:
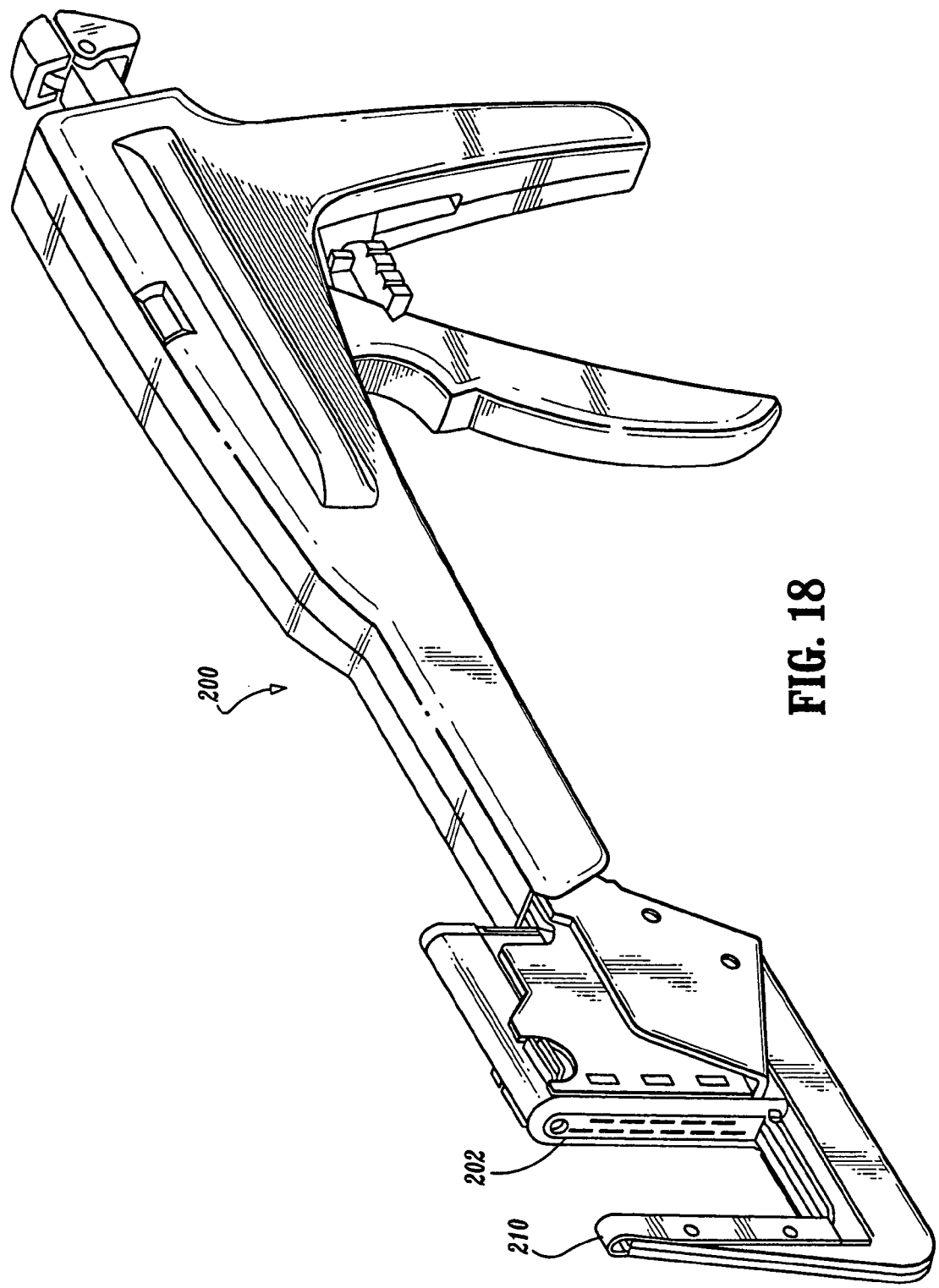
FIG. 18 is a perspective view of a transverse anastomosis-type device for firing the staple of FIG. 5.
Figure 18A:
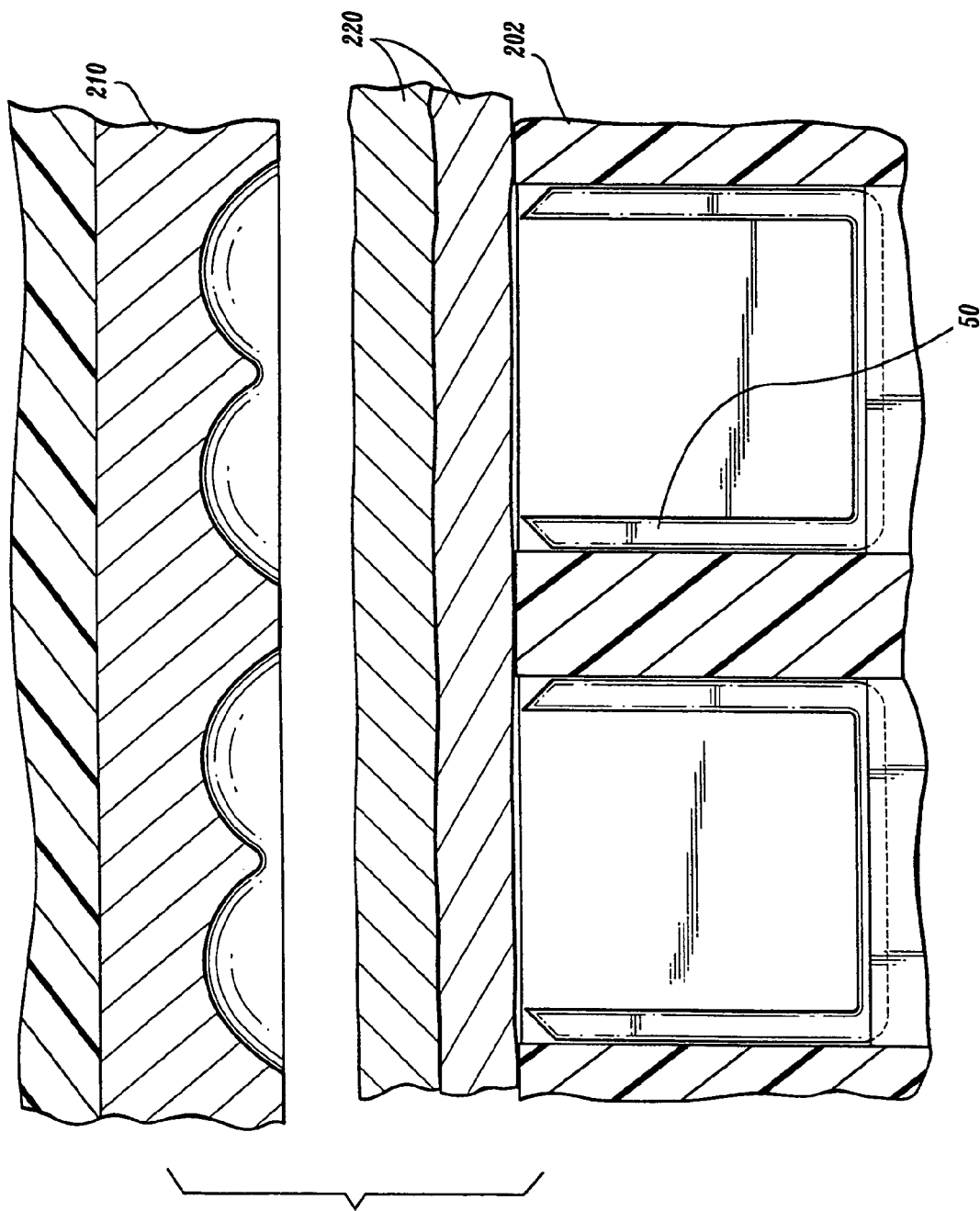
FIG. 18A is an enlarged view of the staple forming anvil and a portion of the disposable loading unit of the device of FIG. 18.
Figure 18B:
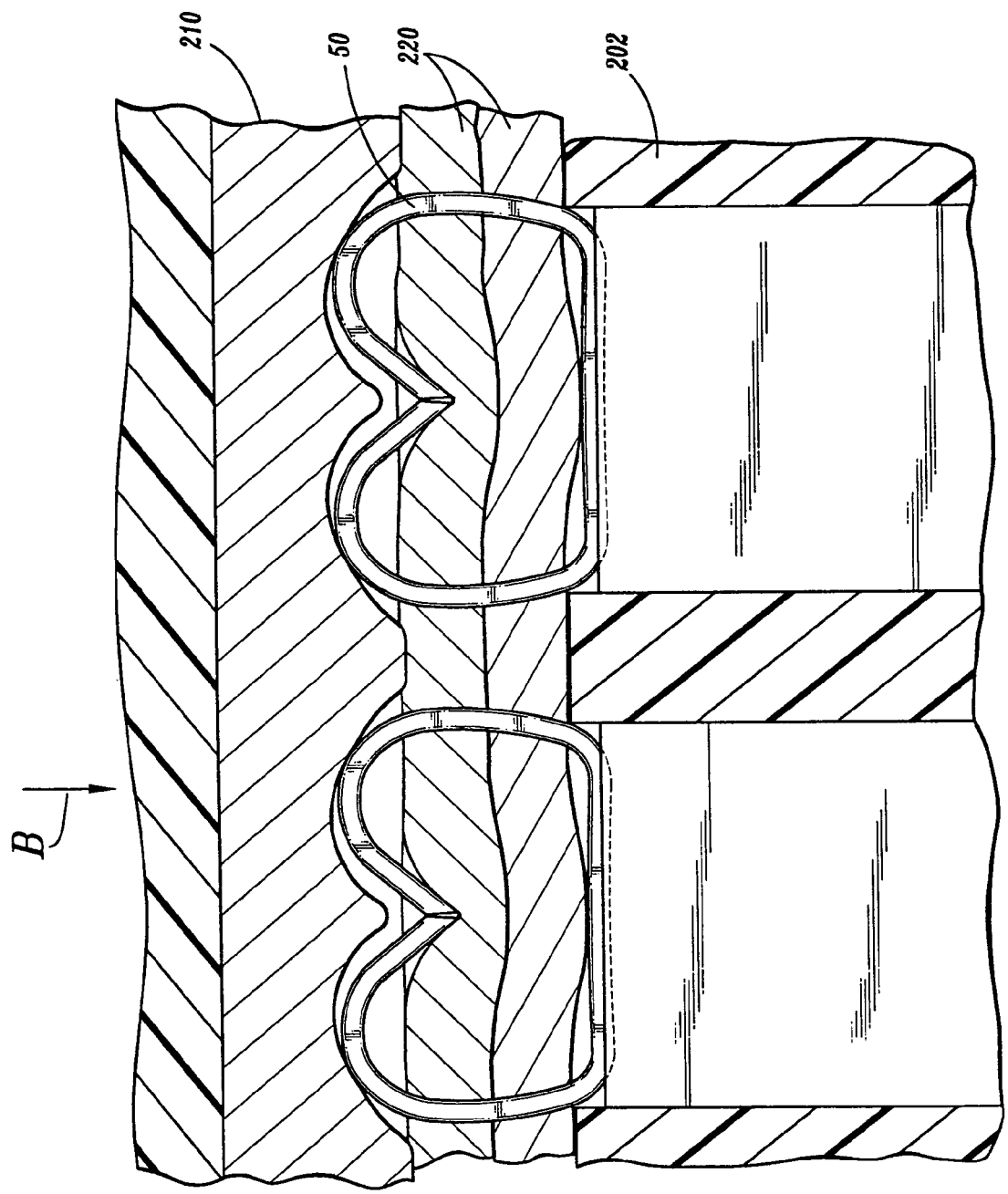
FIGS. 18B and 18C are enlarged views showing the staple formation by the anvil pockets of the instrument of FIG. 18A.
Figure 18C:
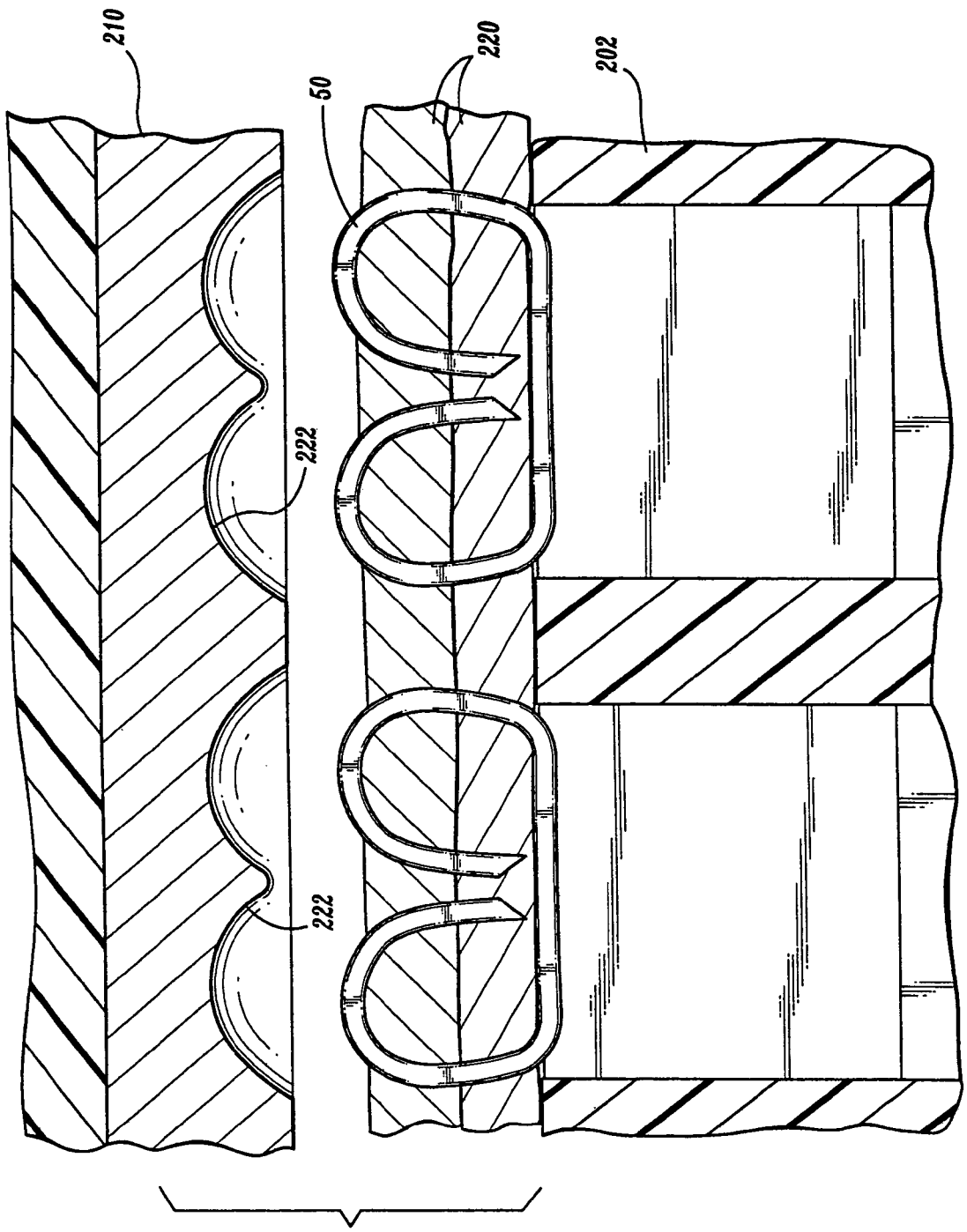

FIG. 18 illustrates a known transverse type surgical stapler 200 including an anvil 210 and a staple cartridge 202 having novel directionally biased staples 50 loaded into the staple cartridge 202. Referring to FIGS. 18A-18C, with anvil 210 and staple cartridge 202 in an open position, tissue 220 is positioned therebetween (FIG. 18A). Anvil 210 is now moved in the direction indicated by arrow "B" to an approximated position towards cartridge 202 (FIG. 18B) in a known manner to compress tissue 220 between anvil 210 and staple cartridge 202. Thereafter, staples 50 are ejected from staple cartridge 202 into pockets 222 formed on anvil 210. Pockets 222 deform staples 50 into a substantially B-shaped configuration (FIG. 18C). Anvil 210 can now be moved to the open position to permit tissue 220 to be removed from stapler 200.

Figure 19:
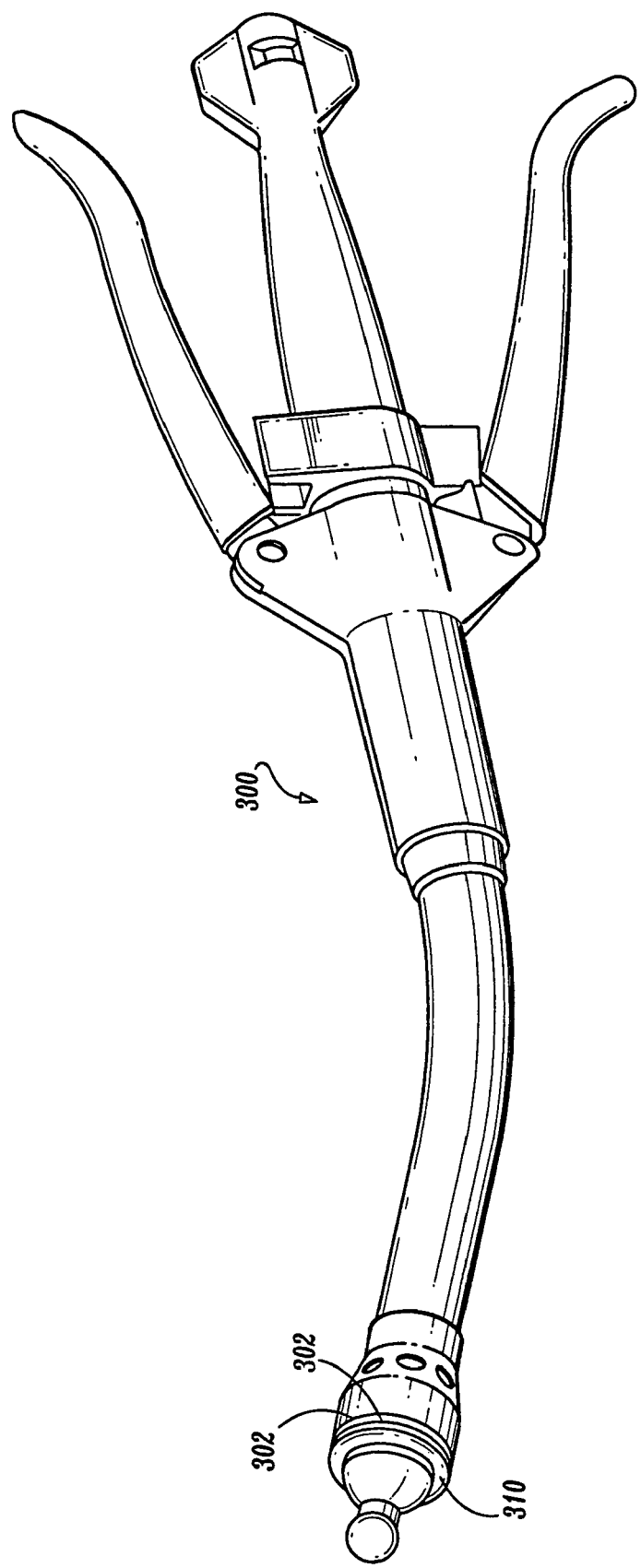
FIG. 19 is a perspective view of a circular anastomosis-type device for firing the staple of FIG. 5.
Figure 19A:
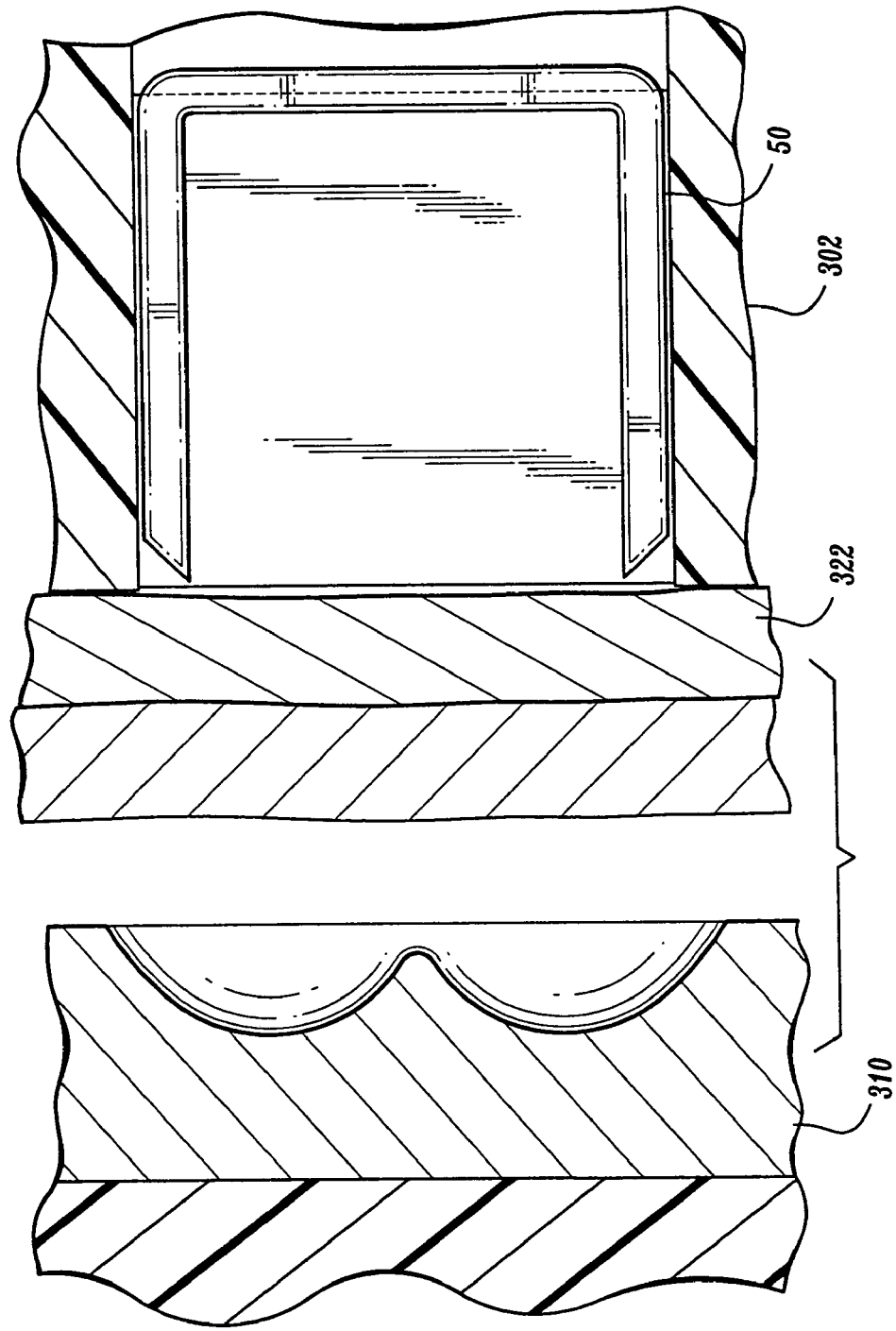
FIG. 19A is an enlarged view of the staple forming anvil and a portion of the disposable loading unit of the device of FIG. 19.
Figure 19B:
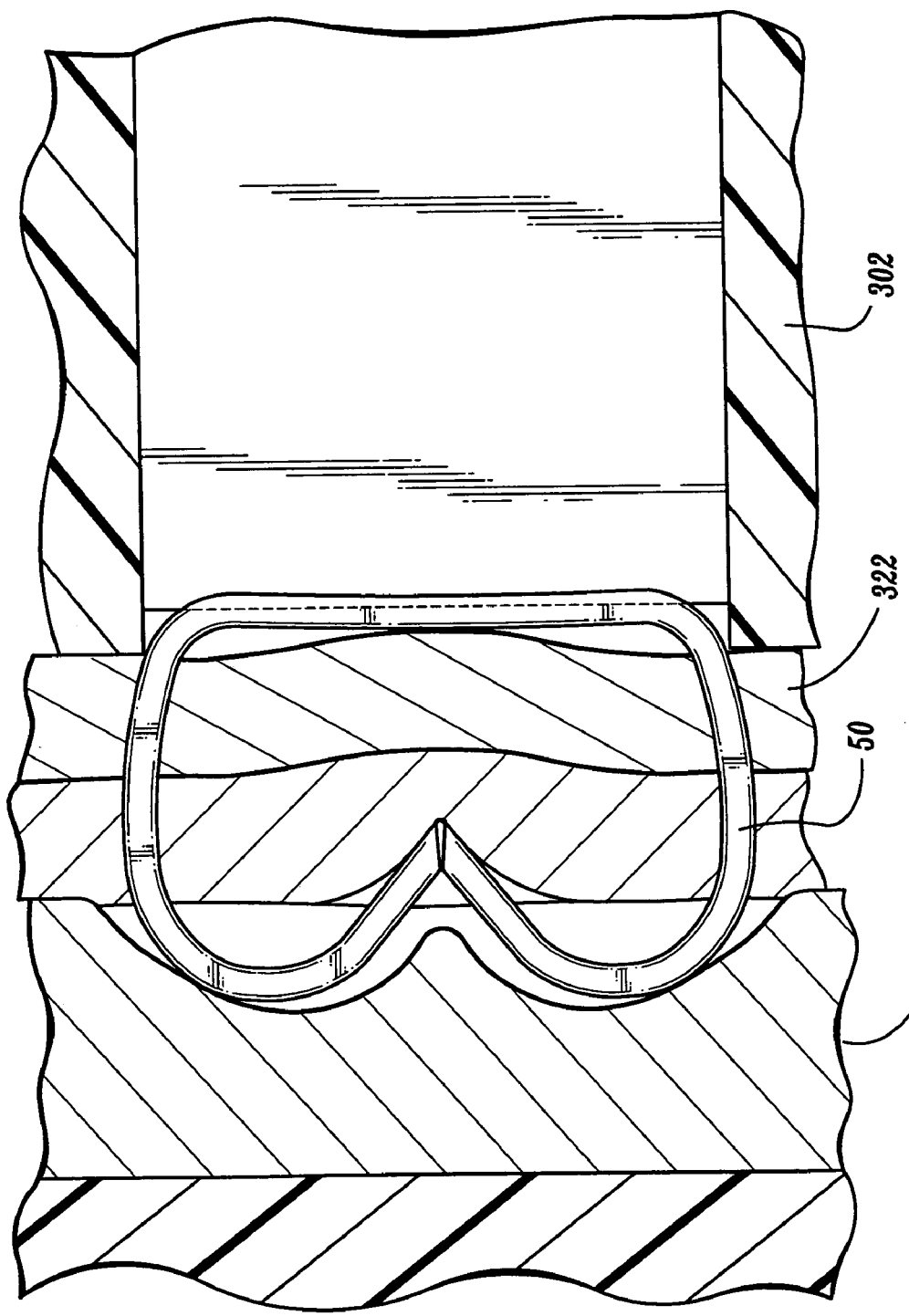

FIG. 19 illustrates a circular stapler 300 including an anvil 310 and a staple cartridge 302 having the novel directionally biased staples 50 loaded in the staple cartridge 302. Referring to FIGS. 19A-19C, with anvil 310 and staple cartridge 302 in an open position, tissue 320 is positioned therebetween (FIG. 19A). Anvil 310 is now moved towards cartridge 302 in a known manner to compress tissue 320 between anvil 310 and staple cartridge 302 (FIG. 19B). Thereafter, staples 50 are ejected from staple cartridge 302 into pockets 322 formed on anvil 310. Pockets 322 deform staples 50 into a substantially B-shaped configuration (FIG. 19C). Anvil 110 can now be moved to the open position to permit tissue 320 to be removed from stapler 300.

Figure 29:
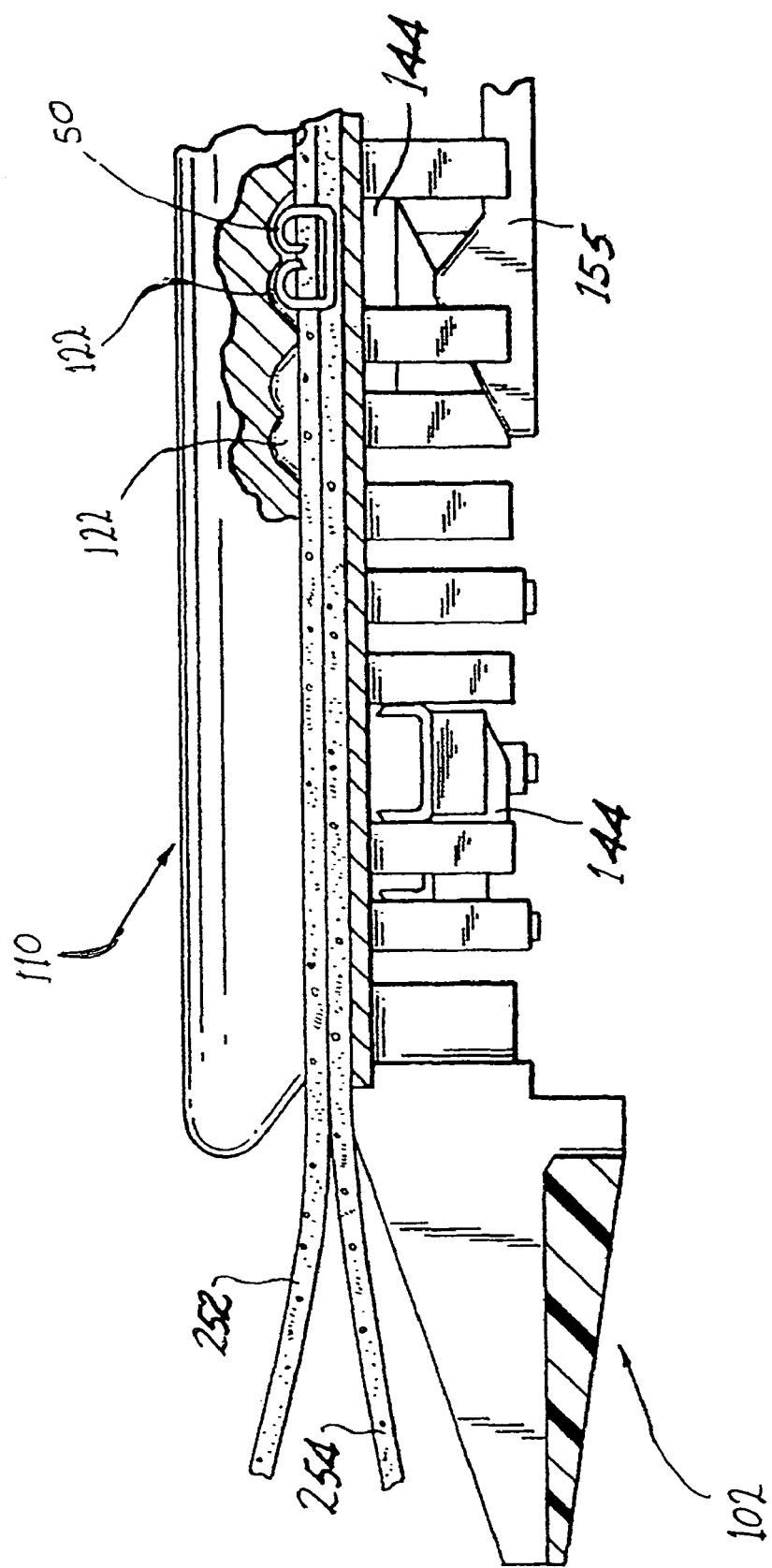
FIG. 29 illustrates a side view in partial cross section of a staple cartridge and anvil in accordance with an embodiment of the present disclosure.

With reference to FIG. 29, an embodiment of staple cartridge 102 of the present disclosure includes pusher elements or staple drivers 144, and surgical fasteners or staples 50. The staples 50 and staple drivers 144 are disposed such that as cam bars 155 move distally and longitudinally through staple cartridge 102, staple drivers 144 drive staples 50 through body tissue layers 252 and 254 which are to be joined, and against anvil 110 where the legs of the staples 50 are crimped in pockets 122.

Figures 20, 21:
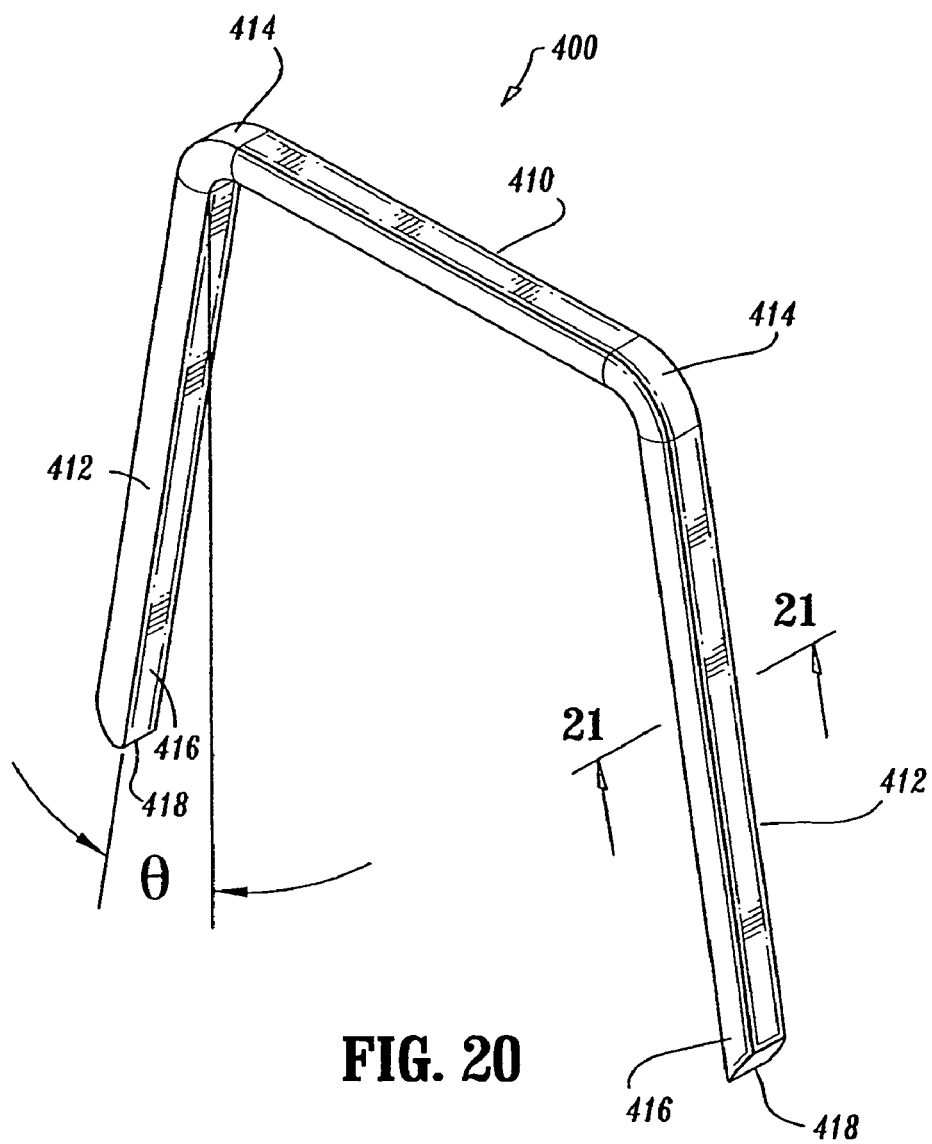
FIG. 20 is a perspective view of another embodiment of a directionally biased staple in accordance with the present disclosure.
FIG. 21 is a cross-sectional view taken along section lines 21-21 of FIG. 20.

FIGS. 20-23 illustrate another preferred embodiment of the presently disclosed directionally biased staple shown generally as 400. Directionally biased staple 400 includes a crown portion 410 and a pair of outwardly angled legs 412 with a bending region 414. Legs 412 define an angle about 5° to about 15° with crown portion 410. Preferably, legs 412 define an angle of about 9° with respect to crown portion 410. Alternately, other angle orientations are envisioned. The angle of legs 412 function to retain the staple within staple receiving slots of a staple cartridge prior to use, i.e., legs 412 frictionally engage the slot walls of a staple cartridge to retain the staple within a cartridge slot. Tissue penetrating portions 416 are formed at the distal end of legs 412 and preferably have a chisel shape with points 418 adjacent inner facing sides of legs 412. Referring to FIG. 21, staple 400 has a cross-section having flat top and bottom surfaces 420 and 422 and semi-circular side surfaces 424 and 426. Preferably, this cross-section is achieved by rolling top and bottom surfaces of wire stock. Alternately, other methods including extrusion and coining may be used to form staple 400. Using the appropriate formulas, the Moment of Inertia ratio of staple 400 is approximately 2. Alternately, the dimensions of staple 400 may be varied in a manner to achieve a Moment of Inertia ratio within the preferred range of about 1.1 to about 3.

Figure 22:
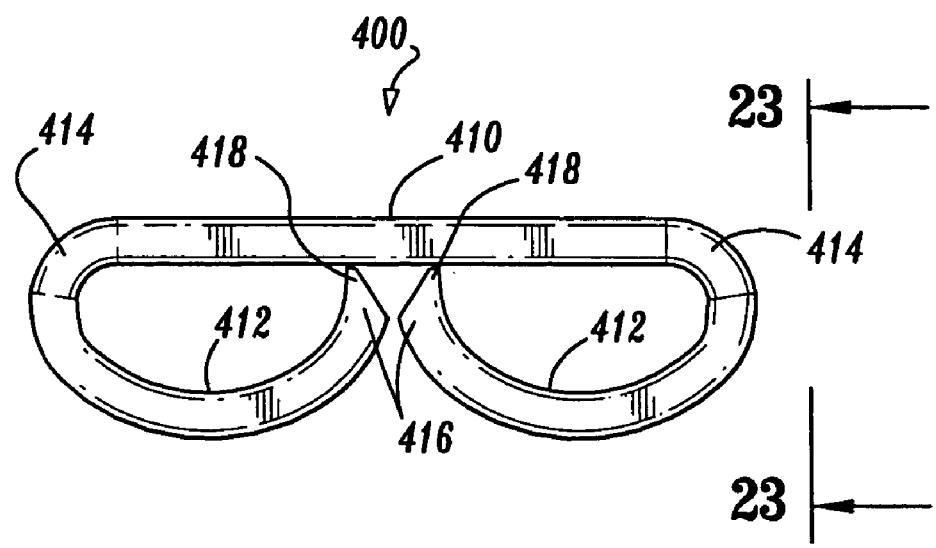
FIG. 22 is a front elevational view of the directionally biased staple shown in FIG. 20 after the staple has been deformed to the B-shaped configuration.
Figure 23:
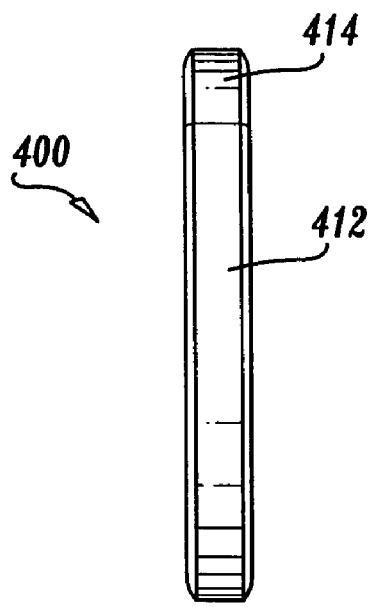
FIG. 23 is a side elevational view from the direction of lines 23-23 of FIG. 22.
Figure 24:
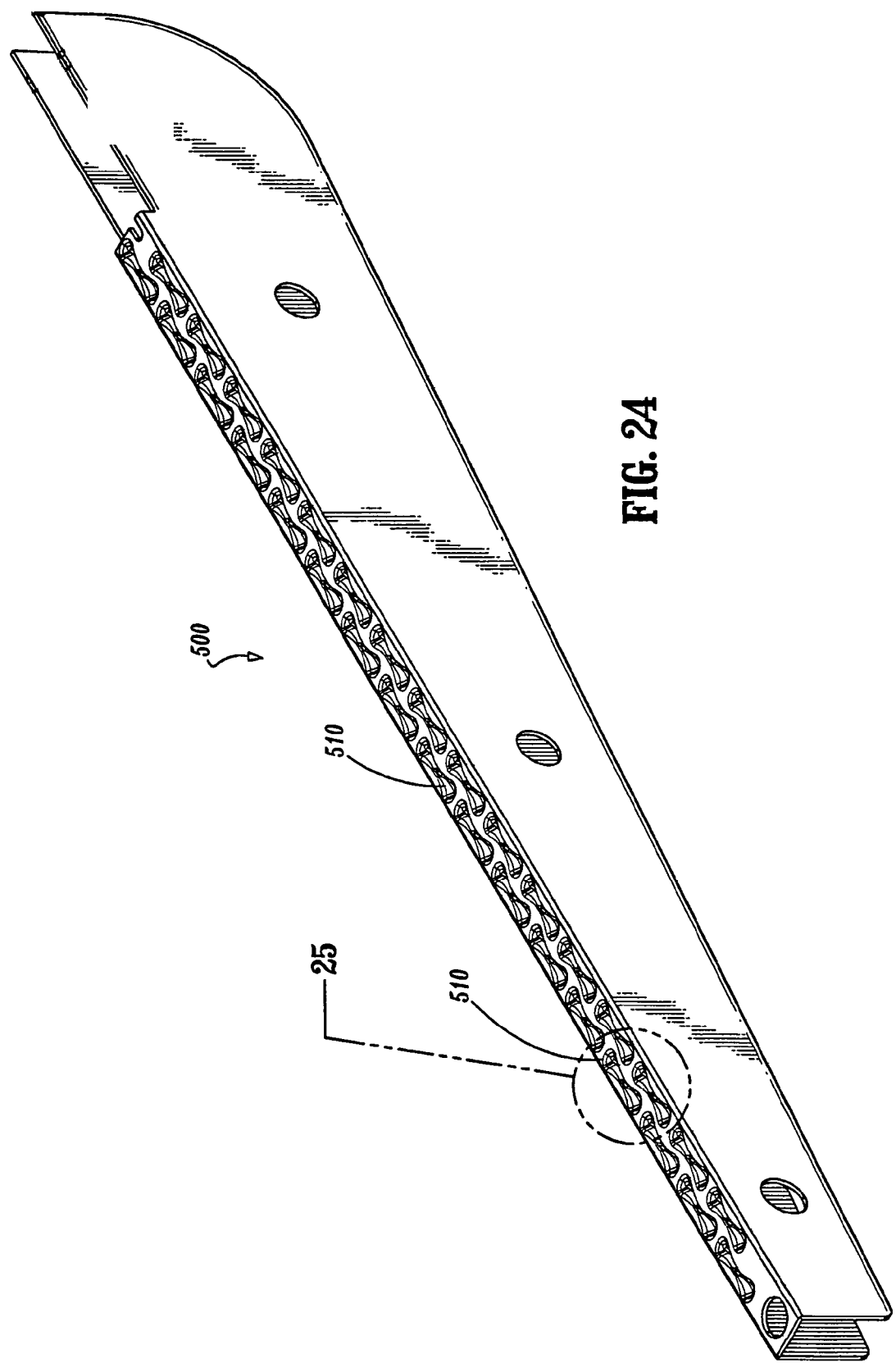
FIG. 24 is a perspective view of an anvil adapted for attachment to an endoscopic gastrointestinal anastomosis-type device.
Figure 25:
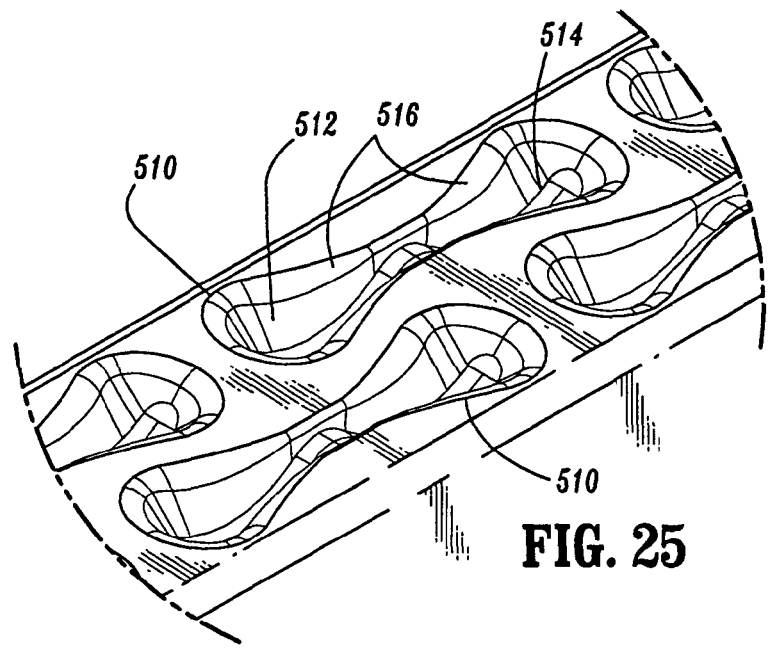
FIG. 25 is an enlarged view of the indicated area of detail shown in FIG. 24.
Figure 26:
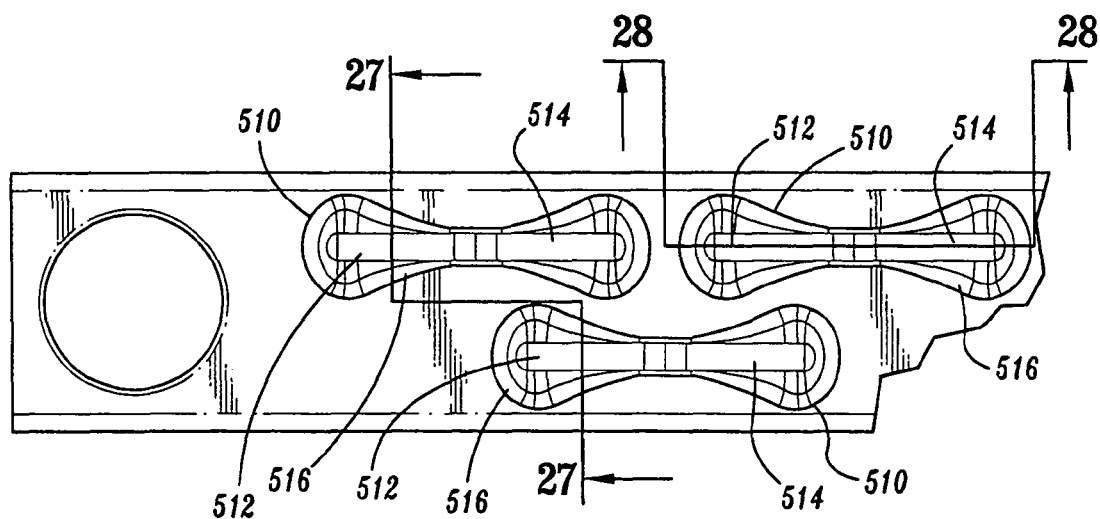
FIG. 26 is a top partial cutaway view of the anvil shown in FIG. 24.
Figure 27:
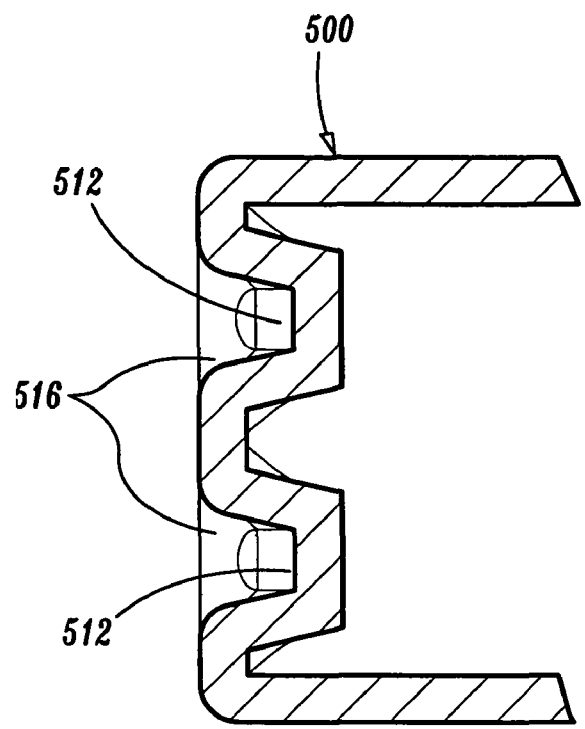
FIG. 27 is a cross-sectional view taken along section lines 27-27 of FIG. 26.
Figure 28:
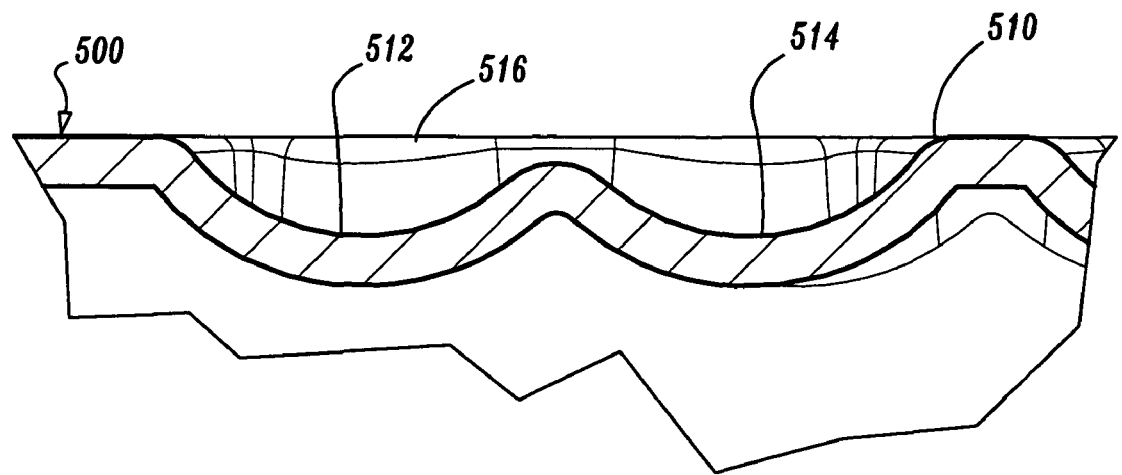
FIG. 28 is a cross-sectional view taken along section lines 28-28 of FIG. 26.

FIGS. 22 and 23 illustrate staple 400 in the formed state wherein staple 400 assumes a B-shaped configuration. FIGS. 24-28 illustrate an anvil 500 which is configured for attachment to a transverse-type surgical stapler such as shown in FIG. 18. Anvil 500 includes a plurality of staple pockets 510 formed in the surface of the anvil. Each staple pocket 510 includes first and second staple forming cups 512 and 514 and a channeling surface 516 disposed around each of the staple forming cups. An anvil including such a staple forming pocket has been disclosed in U.S. Pat. No. 5,480,089 filed Aug. 19, 1994, the entirety of which is incorporated herein by reference. Anvil 500, including staple forming cups 512 and 514 and channeling surface 516 can be adapted for use with any of the surgical stapling devices described in the specification above including endoscopic gastrointestinal anastomosis-type devices (FIG. 15), gastrointestinal anastomosis-type devices (FIG. 17), transverse anastomosis-type devices (FIG. 18) and circular anastomosis-type devices (FIG. 19).

There are various methods of manufacture of the surgical staple. For example, the method could include the steps of flat rolling the wire stock to form at least one flat surface thereon and cutting a length of round wire stock to a predetermined length corresponding to a desired length of a finished staple or extruding the stock with a flat surface. The stock is bent into a form having a backspan and a pair of legs wherein the staple has an aspect ratio of between about 1.1 to about 3.0.

Although a specific embodiment of the present disclosure has been described above in detail, it will be understood that this description is merely for purposes of illustration. Various modifications of and equivalent structures corresponding to the disclosed aspects of the preferred embodiment in addition to those described above may be made by those skilled in the art without departing from the spirit of the present disclosure which is defined in the following claims, the scope of which is to be accorded the broadest interpretation so as to encompass such modifications and equivalent structures. For example the anvil shown and described in U.S. Pat. No. 5,480,089, the contents of which are incorporated herein by reference, can also be utilized.

What is claimed is:

1. A cartridge for use with a surgical stapler, the cartridge having a plurality of individual directionally biased surgical staples therein and associated pushers for ejecting the staples from the cartridge, each of the staples being supported within the cartridge in spaced relation from adjacent staples and each of the staples comprising:
a backspan;
a pair of deformable legs depending from the backspan, the legs configured to come into contact with anvil pockets for formation of the staple;
each leg including a bending region, the bending region having a base dimension and a height dimension, the base dimension being greater than the height dimension, wherein the bending region defines a moment of inertia ratio of between about 1.1 and about 3.0; and
wherein the bending region has a substantially uniform cross-section along substantially the length of the pair of deformable legs.

2. The cartridge of claim 1, wherein the bending region is substantially rectangular in cross-section.

3. The cartridge of claim 1, wherein the bending region is substantially oblate in cross-section.

4. The cartridge of claim 3, wherein each of the staples is formed from a material selected from the group consisting of titanium and stainless steel.

5. The cartridge of claim 1, wherein the bending region is formed of titanium and has a moment of inertia ratio of between about 2.0 and about 2.7.

6. The cartridge of claim 1, wherein the bending region is formed of stainless steel and has a moment inertia ratio of between about 2.0 and about 2.7.

7. The cartridge of claim 1, wherein the bending region is formed in a shape corresponding substantially to the group of shapes consisting of an ellipse, a trapezoid, a triangle and a semicircle.

8. The cartridge of claim 1, further comprising a penetrating structure formed on a distal end portion of at least one of the legs.

9. The cartridge of claim 8, wherein the penetrating structure is a pointed tip on an inner side of the leg.

10. The cartridge of claim 8, wherein the bending region of the staple is formed in a shape corresponding substantially to the group of shapes consisting of an ellipse, a trapezoid, a triangle and a semicircle.

11. The cartridge of claim 8, wherein each of the staples is formed from a material selected from the group consisting of titanium and stainless steel.

12. The cartridge of claim 1, wherein the staple legs are substantially straight along their length.

13. The cartridge of claim 1, wherein each of the legs has a distal end formed in a chisel shape with a point adjacent an inner side of the leg.

14. A cartridge including a plurality of individual surgical staples, each surgical staple having first and second deformable legs and being deformable by contact of the legs with anvil pockets of an anvil, each of the staples being supported in spaced relation from adjacent staples within the cartridge and comprising:
a backspan;
the first and second deformable legs depending from the backspan, the legs configured to be driven through tissue and into contact with anvil pockets of an anvil;
the backspan and legs configured to have a moment of inertia ratio of between about 1.1 and about 3.0; and
wherein each of the staples having a substantially uniform cross-section along substantially the entire length of each leg.

15. The cartridge of claim 14, wherein the staple includes a bending portion having a base dimension and a height dimension, the base dimension being greater than the height dimension.

16. The cartridge of claim 15, wherein the staples are formed from a material selected from the group consisting of titanium and stainless steel.

17. The cartridge of claim 14, wherein at least a portion of the staple legs has a substantially rectangular cross-section.

18. In a cartridge for use with a surgical stapler having an anvil including a plurality of staple forming pockets and being movably positioned adjacent the cartridge between open and closed positions, the improvement comprising a plurality of individual directionally biased surgical staples each supported within a respective pocket in the cartridge, each of the staples being spaced from adjacent staples in the cartridge and having a backspan and a pair of deformable legs depending from the backspan, the legs having a penetrating portion configured to come into contact with the anvil pockets for formation of the staple and each staple deformable leg including a bending region, the bending region having a base dimension and a height dimension, the base dimension being greater than the height dimension, wherein the bending region has a moment of inertia ratio of between about 1.1 and about 3.0 and wherein the penetrating portion has a chisel shape having an edge positioned at a distal end of the penetrating portion on an inner facing wall of each of the legs.

19. A directionally biased surgical staple for use with a surgical stapler having an anvil including a plurality of anvil pockets, the directionally biased staple comprising:
- a backspan having first and second ends and defining a longitudinal axis; and
- a pair of deformable legs depending from the first and second ends of the backspan, each of the legs diverging outwardly from the other leg and forming an angle θ with respect to an axis perpendicular to the longitudinal axis of the backspan, the deformable legs having substantially uniform dimensions over substantially their entire length;
- wherein each of the legs includes a bending region having a base dimension and a height dimension, the base dimension being greater than the height dimension, wherein the bending region has a moment of inertia ratio of between about 1.1 and about 3.0 and wherein the backspan is substantially linear along at least a majority of its length in an undeformed condition.

20. The directionally biased surgical staple of claim 19, wherein the angle θ is between about 5 degrees and 15 degrees.

21. The directionally biased surgical staple of claim 20, wherein the staple receiving slots are spaced from adjacent staple receiving slots.

22. The directionally biased surgical staple of claim 20, wherein the angle θ is about 9 degrees.

23. The directionally biased surgical staple of claim 19, wherein each of the legs includes a sharp tip.

24. The directionally biased surgical staple of claim 19, wherein the staple is formed from a material selected from the group consisting of titanium and stainless steel.

25. The directionally biased surgical staple of claim 19, wherein the bending region has a moment of inertia ratio of between about 2.0 and about 2.7.

26. The directionally biased surgical staple of claim 19, wherein the staple is positioned within a staple receiving slot of a cartridge, the cartridge including a plurality of said staple receiving slots, one said staple being positioned within each staple receiving slot of the cartridge.

27. The directionally biased surgical staple of claim 19, wherein the legs have a length which is greater than a length of the backspan.

28. A cartridge for use with a surgical stapler, the cartridge comprising:
- a plurality of individually directionally biased surgical staples supported within the cartridge in spaced relation to adjacent directionally biased surgical staples and a plurality of pushers, each of the pushers being associated with one or more of the directionally biased surgical staples for ejecting the directionally biased surgical staples from within the cartridge, each of the directionally biased surgical staples including a backspan and a pair of deformable legs, each of the deformable legs having a bending region including a base dimension and a height dimension, wherein the base dimension is greater than the height dimension such that the bending region has a moment of inertia ratio of between about 2.0 and about 2.7, wherein the bending region has a substantially uniform cross-section along at least a majority of each leg and wherein the distal end portion of each of the pair of deformable legs includes penetrating structure and each of the directionally biased surgical staples is formed from a material selected from the group consisting of titanium and stainless steel.

* * * * *